United States Patent
Gray et al.

(10) Patent No.: US 10,875,844 B2
(45) Date of Patent: Dec. 29, 2020

(54) SALICYLATE INHIBITORS OF MELK AND METHODS OF USE

(71) Applicant: Dana-Farber Cancer Institute, Inc., Boston, MA (US)

(72) Inventors: Nathanael Gray, Boston, MA (US); Tinghu Zhang, Brookline, MA (US); Hai-Tsang Huang, Boston, MA (US); Yubao Wang, Newton, MA (US); Jean Zhao, Brookline, MA (US); Hwan Geun Choi, Seoul (KR)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/554,753

(22) PCT Filed: Mar. 4, 2016

(86) PCT No.: PCT/US2016/020858
§ 371 (c)(1),
(2) Date: Aug. 31, 2017

(87) PCT Pub. No.: WO2016/141279
PCT Pub. Date: Sep. 9, 2016

(65) Prior Publication Data
US 2018/0170912 A1    Jun. 21, 2018

Related U.S. Application Data

(60) Provisional application No. 62/128,258, filed on Mar. 4, 2015.

(51) Int. Cl.
| | |
|---|---|
| *A61K 31/337* | (2006.01) |
| *A61K 31/55* | (2006.01) |
| *C07D 403/12* | (2006.01) |
| *C07D 401/14* | (2006.01) |
| *C07D 223/16* | (2006.01) |
| *C07D 403/14* | (2006.01) |
| *C07D 401/12* | (2006.01) |
| *C07D 413/12* | (2006.01) |
| *C07D 231/12* | (2006.01) |
| *A61P 35/00* | (2006.01) |

(52) U.S. Cl.
CPC ......... *C07D 403/12* (2013.01); *A61K 31/337* (2013.01); *A61K 31/55* (2013.01); *A61P 35/00* (2018.01); *C07D 223/16* (2013.01); *C07D 231/12* (2013.01); *C07D 401/12* (2013.01); *C07D 401/14* (2013.01); *C07D 403/14* (2013.01); *C07D 413/12* (2013.01)

(58) Field of Classification Search
None
See application file for complete search history.

(56) References Cited

U.S. PATENT DOCUMENTS

| | | |
|---|---|---|
| 4,916,145 A | 4/1990 | Tilley et al. |
| 5,801,170 A | 9/1998 | Gaster et al. |
| 6,403,584 B1 | 6/2002 | de Laszlo et al. |
| 2008/0176822 A1 | 7/2008 | Chen |
| 2011/0275797 A1 | 11/2011 | Yokotani et al. |
| 2013/0310391 A1 | 11/2013 | Dorsch et al. |
| 2018/0170912 A1 | 6/2018 | Gray et al. |

FOREIGN PATENT DOCUMENTS

| | | |
|---|---|---|
| WO | WO-2004/043925 A2 | 5/2004 |
| WO | WO-2006/057845 A1 | 6/2006 |
| WO | WO-2006/104141 A1 | 10/2006 |
| WO | WO-2012/028629 A1 | 3/2012 |

OTHER PUBLICATIONS

STN Registry database entry for CAS RN 1348386-07-1, Entered STN Dec. 4, 2011, Accessed Aug. 29, 2018.*
STN Registry database entry for CAS RN 1237516-84-5, entry date Aug. 20, 2010, Accessed Mar. 4, 2019.*
Ito et al. in Cancer Science 94(1), 3-8 (2003).*
STN Registry database entry for CAS RN 1237519-13-9, entry date Aug. 20, 2010, Accessed Jun. 4, 2019.*
STN Registry database entry for CAS RN 1350113-58-4, entry date Dec. 7, 2011, Accessed Jun. 4, 2019.*
International Search Report and Written Opinion for International Application No. PCT/US2016/020858 dated Aug. 5, 2016.
Bao et al., "Design and synthesis of biphenyl derivatives as mushroom tyrosinase inhibitors," BioorgMedChem, 18: 6708-6714 (2010).
Johnson et al., "Fragment-Based Discovery of Type I Inhibitors of Maternal Embryonic Leucine Zipper Kinase," MedChemLetters, 6(1): 25-30 (2015).

* cited by examiner

*Primary Examiner* — Samantha L Shterengarts
(74) *Attorney, Agent, or Firm* — Foley Hoag LLP

(57) ABSTRACT

Provided herein are small molecule inhibitors of maternal embryonic leucine zipper kinase (MELK) having the structure of formula (I),

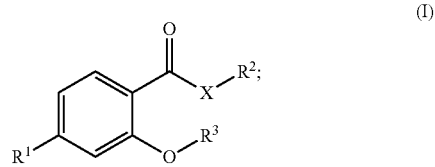

wherein X and $R^1$-$R^3$ are defined in the specification. The compounds are useful for treating cancer and other conditions or diseases associated with aberrant MELK expression. Also provided herein are pharmaceutical compositions comprising a compound of formula (I) and a pharmaceutically acceptable carrier. The invention also provides methods of treating cancers associated with over-expression of MELK.

13 Claims, No Drawings

SALICYLATE INHIBITORS OF MELK AND METHODS OF USE

RELATED APPLICATIONS

This application is the United States National Stage application of PCT/US2016/020858, filed Mar. 4, 2016, which claims the benefit of priority to U.S. Provisional Patent Application Ser. No. 62/128,258, filed Mar. 4, 2015, the contents of which are hereby incorporated by reference.

GOVERNMENT SUPPORT

This invention was made with government support under grant number P50CA168504 awarded by The National Institutes of Health. The government has certain rights in the invention.

BACKGROUND

Despite marked advances in the diagnosis and treatment of breast cancer, patients with basal-like breast cancer (BBC), an aggressive subtype of breast cancer, continue to be confronted with limited treatment options due to current lack of molecular targets in this tumor type. Therefore, the identification of a "druggable" target that is specifically required for basal-like breast tumors is one of the most pressing challenges facing cancer researchers today. The inventors recently identified maternal embryonic leucine zipper kinase (MELK), a novel oncogenic kinase that emerged from an unbiased, in vivo tumorigenesis screen, as a therapeutic target in BBC.

MELK is an atypical member of the AMPK family. While MELK has been implicated in regulating cell cycle progression, cellular proliferation, apoptosis, and mRNA splicing (Badouel et al. (2006) *Cell Cycle* 5:883-889 and Badouel et al. (2010) *Exp. Cell Res.* 316:2166-2173), the exact function of MELK is unknown. MELK is overexpressed in a number of cancers, including cancers of the colon, breast, ovaries, pancreas, prostate, and brain (Gangulu, R., et al. (2014) *Mol. Cancer Ther.* 13(6), 1393-1398). In particular, MELK is highly overexpressed selectively in the BBC subtype. Preliminary data shows that overexpression of wild type MELK induces robust oncogenic transformation both in vitro and in vivo with a transforming potency comparable to that of a highly oncogenic mutant allele of PIK3CA. Even more striking is the finding that only human BBC cells, but not luminal breast cancer cells or normal non-cancerous cells, depend on MELK for proliferation. Notably, the kinase activity of MELK is required for its transforming activity as well as for the survival and proliferation of BBC cells. Thus, MELK is potentially a novel oncogenic driver of basal-like breast carcinoma and a promising target for small molecule-based therapeutic intervention.

Because overexpression of MELK has been associated with a number of cancers, there remains a need to develop small molecule-based therapeutic agents that target MELK and that can be used in the treatment of cancers such as BBC that are specifically dependent on MELK. There also remains a need to develop preclinical models for evaluating the efficacy of candidate therapeutic agents against MELK in vivo, and for assessing on-target effects and side-effects of systemic loss of MELK in vivo.

SUMMARY OF THE INVENTION

In one aspect, the invention relates to a compound represented by formula (I) or a pharmaceutically acceptable salt thereof:

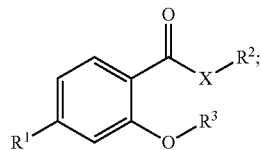

wherein:
$R^1$ represents substituted or unsubstituted heteroaryl or aryl;
$R^2$ represents substituted or unsubstituted aryl, heteroaryl, aralkyl, or heteroaralkyl;
$R^3$ represents substituted or unsubstituted alkyl, cycloalkyl, (cycloalkyl)alkyl, aralkyl, heteroarylalkyl, heterocycloalkyl, (heterocycloalkyl)alkyl, or aminoalkyl, wherein the substituted or unsubstituted alkyl comprises a tertiary or quaternary carbon; and
X represents NH, O, or S.

The invention also relates to pharmaceutical compositions, comprising a compound of formula (I) as a pharmaceutically acceptable carrier.

In another aspect, the invention relates to methods of treating cancer, comprising administering to a subject in need thereof a therapeutically effective amount of a compound of formula (I). In another aspect, the invention relates to methods for treating or preventing a condition associated with aberrant maternal embryonic leucine zipper kinase (MELK).

In another aspect, the invention relates to methods of inhibiting maternal embryonic leucine zipper kinase (MELK), comprising contacting MELK with a compound of formula (I) in an amount effective to inhibit MELK.

In another aspect, the invention relates to methods of decreasing the rate of mitosis in a cancer cell, comprising contacting the cancer cell with a compound of formula (I) in an amount effective to decrease the rate of mitosis of the cancer cell.

DETAILED DESCRIPTION OF THE INVENTION

Maternal embryonic leucine zipper kinase (MELK) is an oncogenic kinase that is over-expressed in a number of cancers, including cancers of the colon, breast, ovaries, pancreas, prostate, and brain. Activation of this kinase is associated with survival and proliferation of cancer stem cells in various organs. Accordingly, inhibition of this kinase presents a therapeutic strategy for the treatment of cancers associated with MELK expression.

The present invention is based, at least in part, on the discovery of a class of small molecule compounds having inhibitory activity for MELK. These compounds exhibit suitable pharmacological properties, which facilitate their use in therapeutic applications.

I. Definitions

The articles "a" and "an" are used herein to refer to one or to more than one (i.e., to at least one) of the grammatical object of the article. By way of example, "an element" means one element or more than one element.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like.

Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive.

For example, substitution of alkynyl groups by one or more alkyl, carbocyclyl, aryl, heterocyclyl, or heteroaryl groups is contemplated.

The term "amide", as used herein, refers to a group

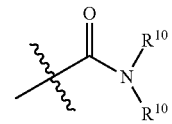

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

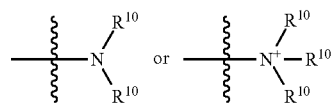

wherein each $R^{10}$ independently represents a hydrogen or a hydrocarbyl group, or two $R^{10}$ are taken together with the N atom to which they are attached complete a heterocycle having from 4 to 8 atoms in the ring structure. In certain embodiments, amine encompasses cyclic amines, including bicyclic amines. In certain embodiments, amine includes DABCO (1,4-diazabicyclo[2.2.2]octane).

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. Substituents of a substituted aryl may include any of the groups contemplated as substituents for alkyl and cycloalkyl groups, which are described herein.

The term "carbamate" is art-recognized and refers to a group

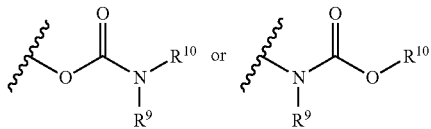

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —$OCO_2$—$R^{10}$, wherein $R^{10}$ represents a hydrocarbyl group.

The term "carboxy", as used herein, refers to a group represented by the formula —$CO_2H$.

The term "ester", as used herein, refers to a group —$C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

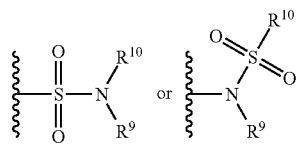

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^{10}$, wherein $R^{10}$ represents a hydrocarbyl. In certain embodiments, the sulfoxide may be a stereogenic center. In certain such embodiments, the compounds may be enriched for one isomer of the sulfoxide.

The term "sulfonate" is art-recognized and refers to the group SO$_3$H, or a pharmaceutically acceptable salt thereof. A sulfonate ester refers to a group —S(O)$_2$—OR$^1$ wherein $R^{10}$ represents a hydrocarbyl.

The term "sulfone" is art-recognized and refers to the group —S(O)$_2$—$R^{10}$, wherein $R^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein $R^{10}$ represents a hydrocarbyl.

The term "thioether", as used herein, is equivalent to an ether, wherein the oxygen is replaced with a sulfur.

The term "disulfide" refers to a group —S—S—$R^{10}$, wherein $R^{10}$ represents a hydrocarbyl.

The term "urea" is art-recognized and may be represented by the general formula

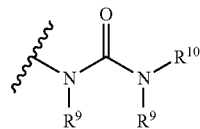

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

The term "tertiary carbon" refers to an $sp^3$-hybridized carbon atom bonded to exactly one hydrogen atom and three non-hydrogen substituents, preferably carbon-based substituents such as alkyl, alkenyl, alkynyl, aryl, aralkyl, heteroaryl, heteroaralkyl, cycloalkyl, heterocyclyl, acyl, carboxy, ester, hydroxyalkyl, haloalkyl, and the like. The term "quaternary carbon" refers to an $sp^3$-hybridized carbon atom bonded to four non-hydrogen substituents, preferably carbon-based substituents such as alkyl, alkenyl, alkynyl, aryl, aralkyl, heteroaryl, heteroaralkyl, cycloalkyl, heterocyclyl, acyl, carboxy, ester, hydroxyalkyl, haloalkyl, and the like.

As used herein, "MELK" refers to the MELK member of the protein kinase superfamily and is alternatively known as "pEG3 kinase," "protein kinase Eg3," "protein kinase," and "serine/threonine-protein kinase MELK." A discussion of the splice variants encoding distinct human MELK isoforms, representative National Center for Biotechnology Information Reference Sequence numbers, and representative DNA and amino acid sequences appear in PCT/US/2014/065173, which is incorporated herein by reference.

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a solid tumor, but such cells may exist alone within an animal, or may be a non-tumorigenic cancer cell, such as a leukemia cell. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In certain embodiments, the cancer is associated with the overexpression of MELK. Also included are any cancers in which the gene encoding MELK is amplified or overexpressed. In certain embodiments, the cancer is breast cancer, ovarian cancer, or melanoma. In certain embodiments, the breast cancer is basal-like breast cancer (BBC).

As used herein, the term "inhibit" includes the decrease, limitation, or blockage, of, for example a particular action, function, or interaction. For example, cancer is "inhibited" if at least one symptom of the cancer, such as hyperproliferative growth, is alleviated, terminated, slowed, or prevented. As used herein, cancer is also "inhibited" if recurrence or metastasis of the cancer is reduced, slowed, delayed, or prevented. An enzyme, for example, a kinase is inhibited if a native biological function of the kinase is reduced, diminished, or stopped.

The term "modulate" includes up-regulation and down-regulation, e.g., enhancing or inhibiting a response.

The term "subject" refers to any healthy animal, mammal or human, or any animal, mammal or human afflicted with a condition of interest (e.g., cancer). The term "subject" is interchangeable with "patient." In other embodiments, the subject has breast cancer, ovarian cancer, or melanoma.

II. Compounds of the Invention

The invention provides compounds according to formula (I), or pharmaceutically acceptable salts thereof;

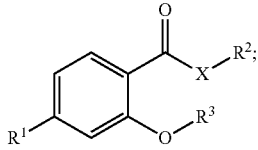
(I)

wherein:
$R^1$ represents substituted or unsubstituted heteroaryl or aryl;
$R^2$ represents substituted or unsubstituted aryl, heteroaryl, aralkyl, or heteroaralkyl;
$R^3$ represents substituted or unsubstituted alkyl, cycloalkyl, (cycloalkyl)alkyl, aralkyl, heteroarylalkyl, heterocycloalkyl, (heterocycloalkyl)alkyl, or aminoalkyl, wherein the substituted or unsubstituted alkyl comprises a tertiary or quaternary carbon; and
X represents NH, O, or S.

In certain embodiments, X is NH.

In certain embodiments, $R^3$ represents substituted or unsubstituted branched alkyl, cycloalkyl, (cycloalkyl)alkyl, aralkyl, heteroarylalkyl, heterocycloalkyl, (heterocycloalkyl)alkyl, or aminoalkyl, wherein the substituted or unsubstituted branched alkyl is branched at the carbon atom bonded to O.

In certain embodiments, $R^3$ represents substituted or unsubstituted cycloalkyl, (cycloalkyl)alkyl, aralkyl, heteroarylalkyl, heterocycloalkyl, or aminoalkyl.

In certain embodiments, $R^3$ is isopropyl, benzyl, cyclohexyl, cyclohexylmethyl, (3-pyridinyl)methyl, or 2,3-dihydro-1H-inden-2-yl. 2,3-dihydro-1H-inden-2-yl is represented by the formula:

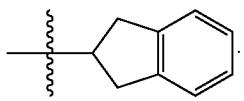 [SMILES: *C1Cc2ccccc2C1]

In certain embodiments, $R^3$ is alkyl, wherein the alkyl is branched at the carbon atom bonded to O, such as in isopropyl, sec-butyl, or tert-butyl.

In certain embodiments, $R^1$ represents substituted or unsubstituted aryl.

In certain embodiments, $R^1$ represents aryl, substituted by one or more substituents selected from the group consisting of $(C_1-C_6)$alkyl, $(C_1-C_6)$alkoxy, aryloxy, aryl$(C_1-C_6)$alkoxy, heteroaryl$(C_1-C_6)$alkoxy, $(C_1-C_6)$haloalkyl, halo, aryl, —$NH_2$, —NH$((C_1-C_6)$alkyl), —N$((C_1-C_6)$alkyl$)_2$, —OH, $(C_3-C_6)$cycloalkyl, $(C_1-C_6)$haloalkoxyl, —SH, —S$((C_1-C_6)$alkyl), $(C_1-C_6)$hydroxyalkyl, $(C_1-C_6)$alkoxy$(C_1-C_6)$alkyl, —CN, —$CF_3$, —C(O)$NH_2$, —C(O)NH$((C_1-C_6)$alkyl), —C(O)N$((C_1-C_6)$alkyl$)_2$, —S(O)$_2NH_2$, —S(O)$_2$NH$((C_1-C_6)$alkyl), —S(O)$_2$N$(((C_1-C_6)$alkyl$)_2$, —NHS(O)$_2$(alkyl), and —NHC(O)$(C_1-C_6)$alkyl).

In certain embodiments, $R^1$ represents aryl, substituted by one or more substituents selected from the group consisting of $(C_1-C_6)$alkyl, $(C_1-C_6)$alkoxy, $(C_1-C_6)$haloalkyl, halo, —OH, $(C_1-C_6)$haloalkoxyl, —SH, —S$((C_1-C_6)$alkyl), $(C_1-C_6)$hydroxyalkyl, and —$CF_3$.

In certain embodiments, $R^1$ is —NHS(O)$_2$(CH$_3$).

In certain embodiments, $R^1$ is represented by:

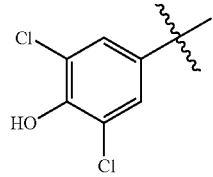

In certain embodiments, $R^1$ represents substituted or unsubstituted heteroaryl. In certain embodiments, $R^1$ is a substituted pyrazolyl, such as

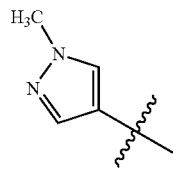

In certain embodiments, $R^1$ represents substituted or unsubstituted pyrrolyl, pyrazolyl, pyridinyl, indazolyl, indolyl, isoquinolinyl, pyrimidinyl, isoxazolyl, oxazolyl, imidazolyl, pyridazinyl, pyrazinyl, benzimidazolyl, benzimidazolonyl, benzothiazolonyl, quinolinyl, quinzolinyl, or quinoxalinyl.

In certain embodiments, $R^1$ represents pyrrolyl, pyrazolyl, pyridinyl, indazolyl, indolyl, isoquinolinyl, pyrimidinyl, isoxazolyl, oxazolyl, imidazolyl, pyridazinyl, pyrazinyl, benzimidazolyl, benzimidazolonyl, benzothiazolonyl, quinolinyl, quinzolinyl, or quinoxalinyl, optionally substituted by one or more substituents selected from $(C_1-C_6)$alkyl, $(C_1-C_6)$alkoxy, $(C_1-C_6)$haloalkyl, halo, —OH, $(C_1-C_6)$haloalkoxyl, —SH, —S$((C_1-C_6)$alkyl), $(C_1-C_6)$hydroxyalkyl, and —$CF_3$.

In certain embodiments, $R^1$ represents 4-pyrazolyl, 5-pyrazolyl, 1-methylpyrazol-4-yl, 1-methylpyrazol-5-yl, 3-pyridinyl, 4-pyradinyl, 1H-indazol-5-yl, 7-isoquinolinyl, 8-isoquinolinyl, 5-pyrimidinyl, or 4-isoxazolyl.

In certain embodiments, $R^2$ represents substituted or unsubstituted aryl or heteroaryl, such as phenyl. In certain embodiments, $R^2$ represents aralkyl, such as benzyl, which may optionally be substituted.

In certain embodiments, $R^2$ represents substituted or unsubstituted 2-pyridinyl, 3-pyridinyl, or 4-pyridinyl.

In certain embodiments, $R^2$ represents aryl, substituted at any one or more substitutable positions by $R^4$, wherein $R^4$ is selected from the group consisting of $(C_1-C_6)$alkyl, $(C_1-C_6)$alkoxy, aryloxy, aryl$(C_1-C_6)$alkoxy, heteroaryl$(C_1-C_6)$alkoxy, $(C_1-C_6)$haloalkyl, halo, aryl, —$NH_2$, —NH$((C_1-C_6)$alkyl), —N$((C_1-C_6)$alkyl$)_2$, amino$(C_1-C_6)$alkoxy, —OH, $(C_3-C_6)$cycloalkyl, $(C_1-C_6)$haloalkoxyl, —SH, —S$((C_1-C_6)$alkyl), $(C_1-C_6)$hydroxyalkyl, $(C_1-C_6)$alkoxy$(C_1-C_6)$alkyl, —CN, —$CF_3$, —C(O)$NH_2$, —C(O)NH$((C_1-C_6)$alkyl), —C(O)N$((C_1-C_6)$alkyl$)_2$, —C(O)NH(aryl), —S(O)$_2NH_2$, —S(O)$_2$NH$((C_1-C_6)$alkyl), —S(O)$_2$N$(((C_1-C_6)$alkyl$)_2$, —NHC(O)(aryl), and —NHC(O)$(C_1-C_6)$alkyl).

Alternatively, in certain embodiments, two adjacent occurrences of $R^4$ can be taken together to form a ring.

In certain embodiments of the invention, R² represents
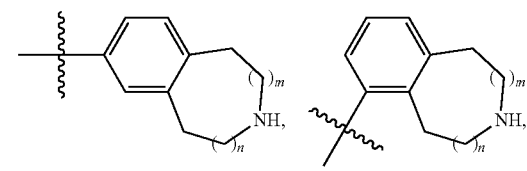
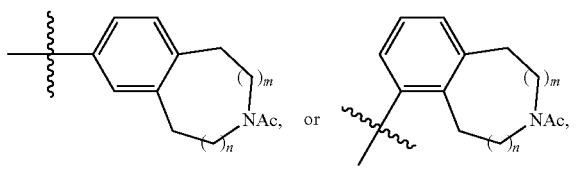
wherein m and n are integers, each independently selected from 0 and 1.
In certain embodiments, the invention provides a compound according to the following table:
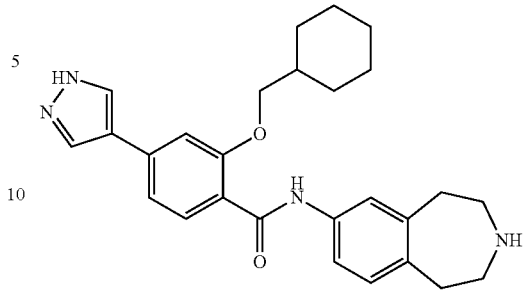
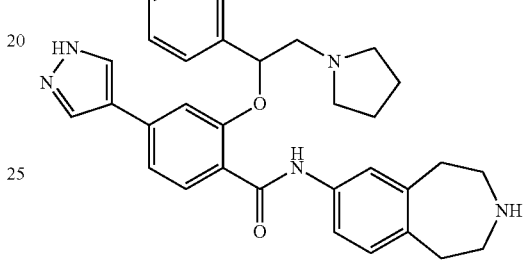
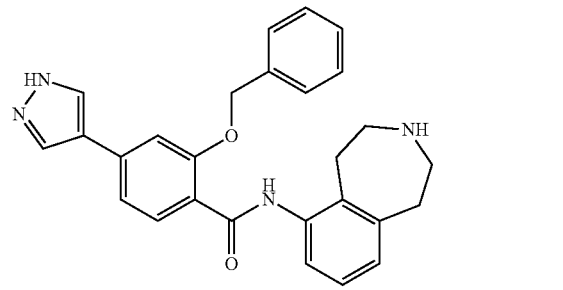 [SMILES: O=C(Nc1cccc2c1CCNCC2)c1ccc(-c2cn[nH]c2)cc1OCc1ccccc1]
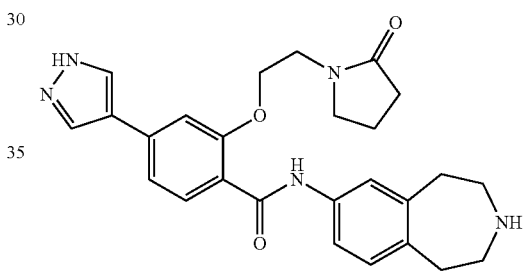
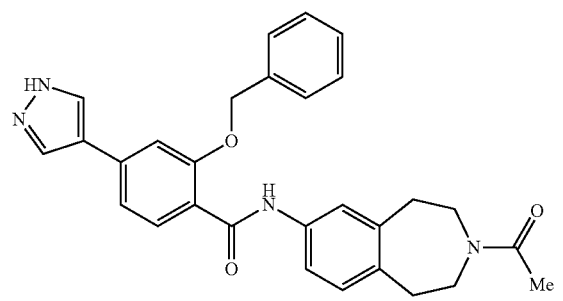 [SMILES: CC(=O)N1CCc2ccc(NC(=O)c3ccc(-c4cn[nH]c4)cc3OCc3ccccc3)cc2CC1]
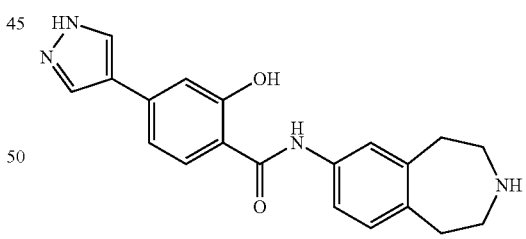
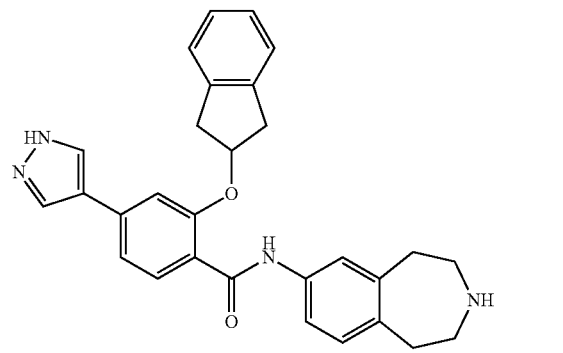 [SMILES: O=C(Nc1ccc2c(c1)CCNCC2)c1ccc(-c2cn[nH]c2)cc1OC1Cc2ccccc2C1]
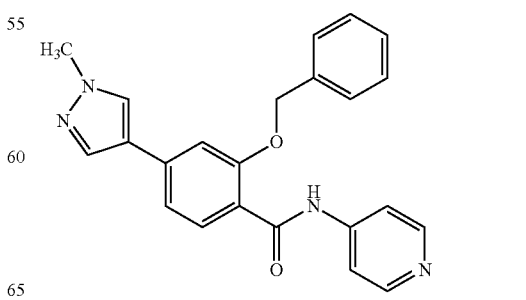

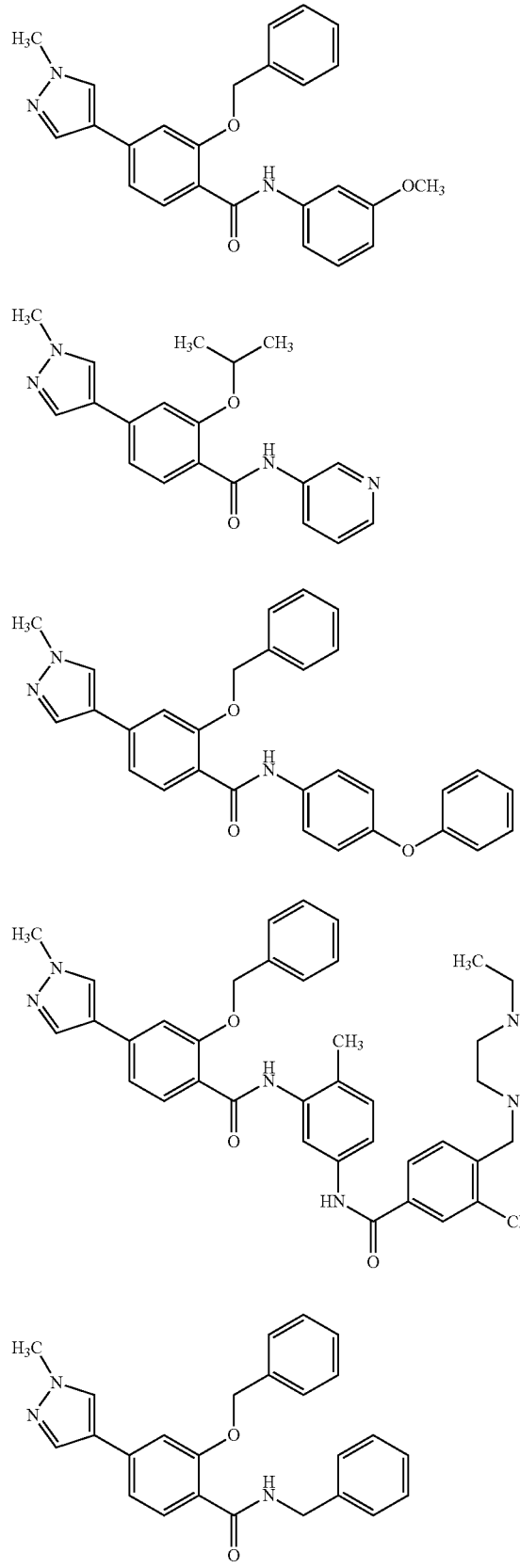
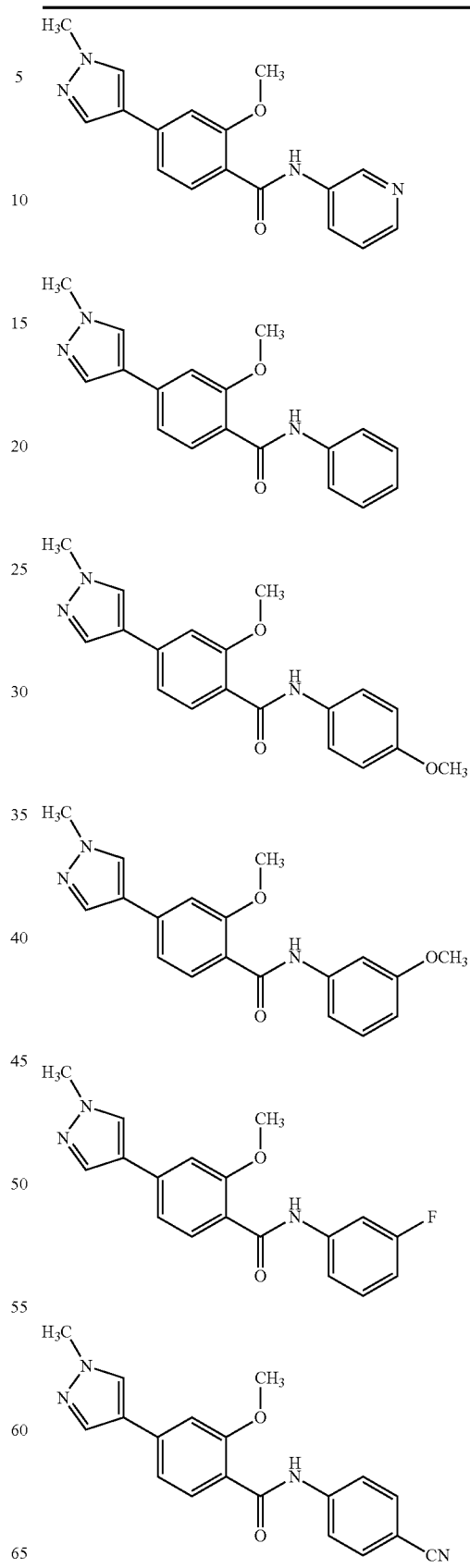

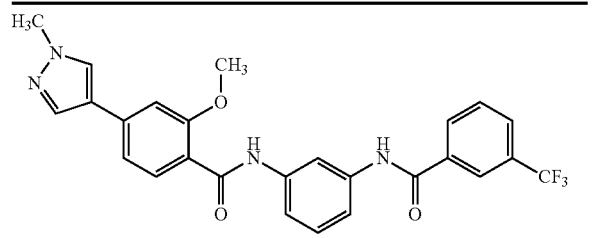
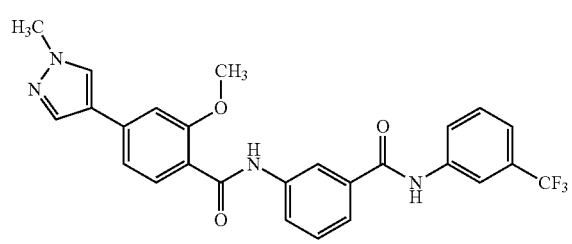 [SMILES: COc1cc(-c2cnn(C)c2)ccc1C(=O)Nc1cccc(C(=O)Nc2cccc(C(F)(F)F)c2)c1]
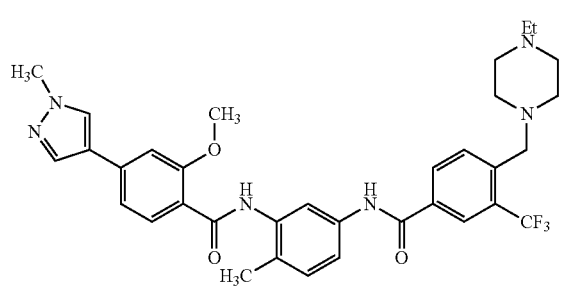
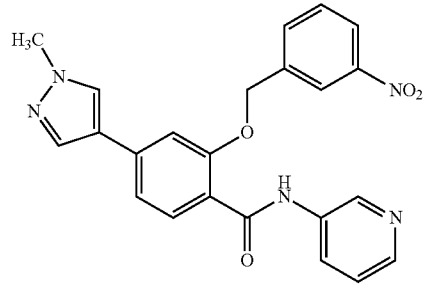 [SMILES: Cn1cc(-c2ccc(C(=O)Nc3cccnc3)c(OCc3cccc([N+](=O)[O-])c3)c2)cn1]
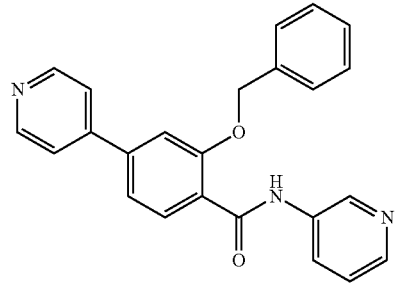 [SMILES: O=C(Nc1cccnc1)c1ccc(-c2ccncc2)cc1OCc1ccccc1]
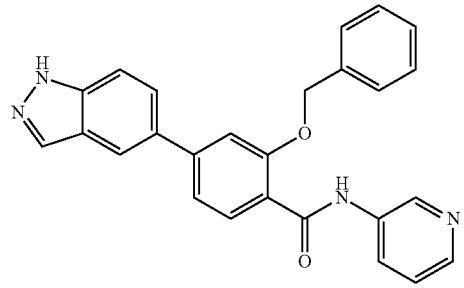 [SMILES: O=C(Nc1cccnc1)c1ccc(-c2ccc3[nH]ncc3c2)cc1OCc1ccccc1]
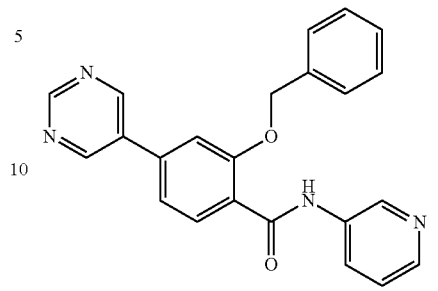
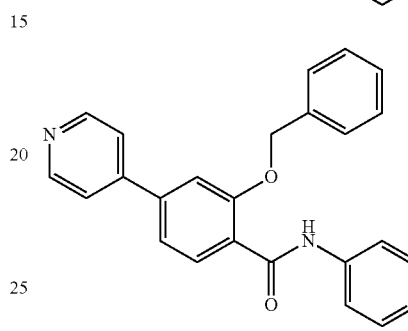
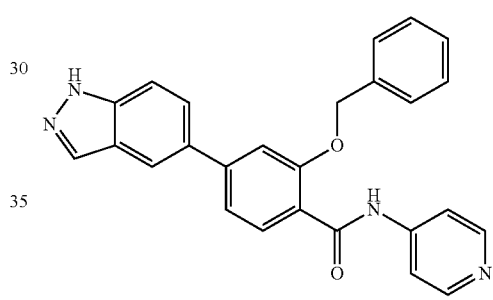
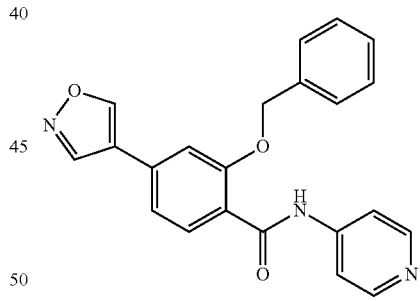
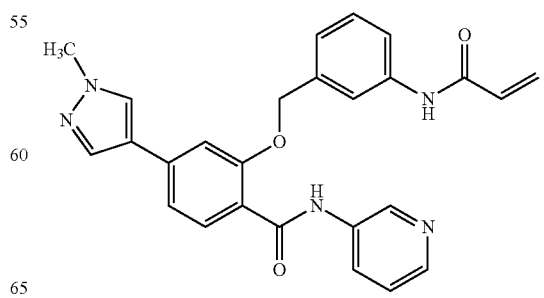

-continued
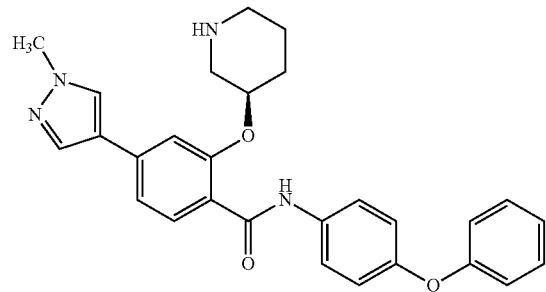 [SMILES: Cn1cc(-c2ccc(C(=O)Nc3ccc(Oc4ccccc4)cc3)c(O[C@@H]3CCCNC3)c2)cn1]
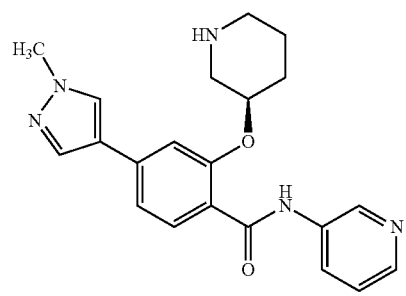 [SMILES: Cn1cc(-c2ccc(C(=O)Nc3cccnc3)c(O[C@@H]3CCCNC3)c2)cn1]
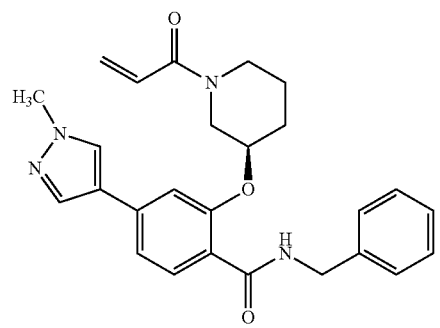 [SMILES: C=CC(=O)N1CCC[C@@H](Oc2cc(-c3cnn(C)c3)ccc2C(=O)NCc2ccccc2)C1]
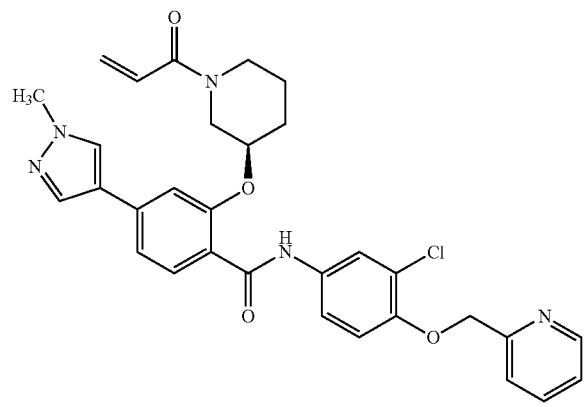 [SMILES: C=CC(=O)N1CCC[C@@H](Oc2cc(-c3cnn(C)c3)ccc2C(=O)Nc2ccc(OCc3ccccn3)c(Cl)c2)C1]
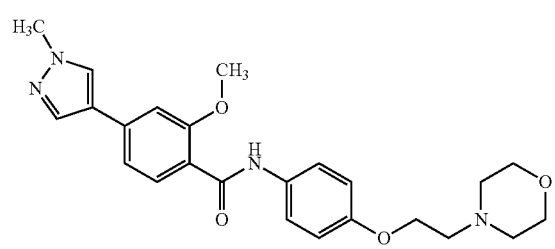 [SMILES: COc1cc(-c2cnn(C)c2)ccc1C(=O)Nc1ccc(OCCN2CCOCC2)cc1]
-continued
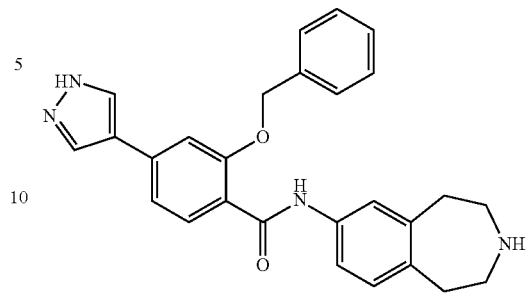
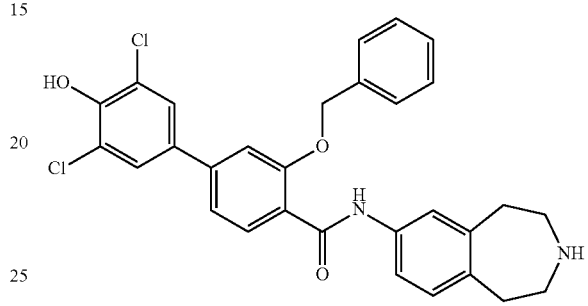
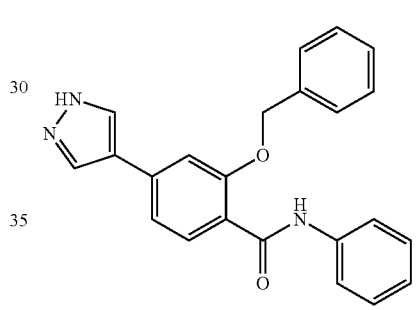
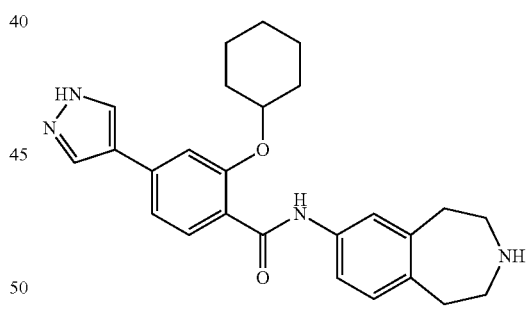
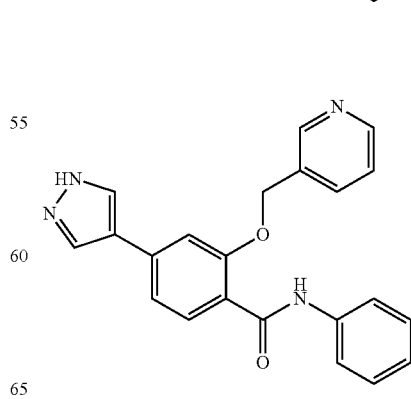

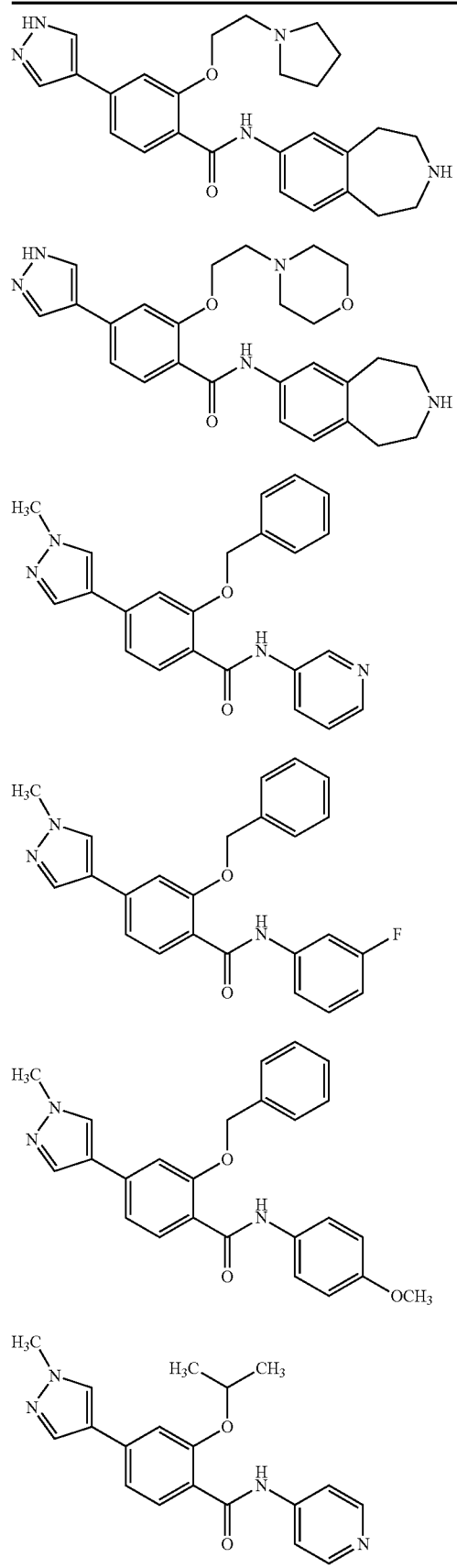
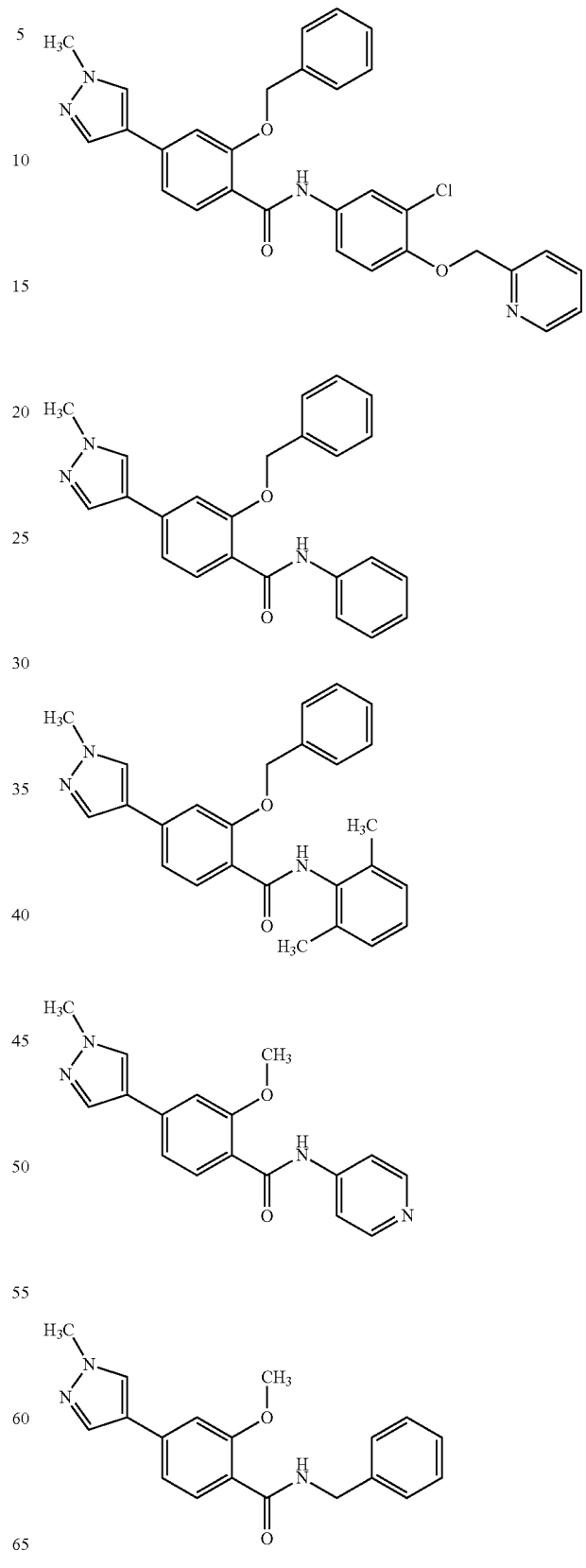

-continued
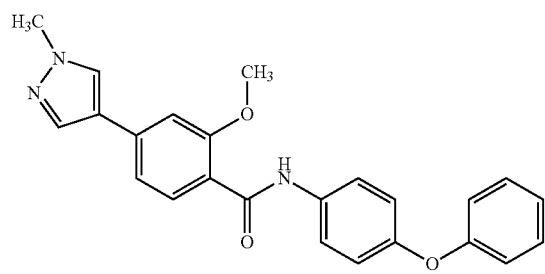 [SMILES: COc1cc(-c2cnn(C)c2)ccc1C(=O)Nc1ccc(Oc2ccccc2)cc1]
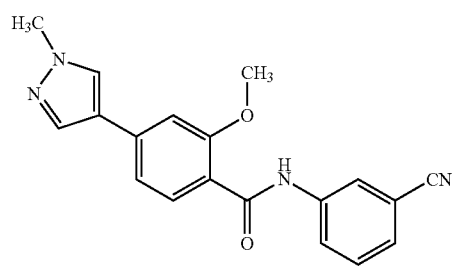 [SMILES: COc1cc(-c2cnn(C)c2)ccc1C(=O)Nc1cccc(C#N)c1]
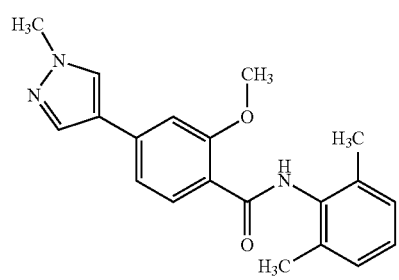 [SMILES: COc1cc(-c2cnn(C)c2)ccc1C(=O)Nc1c(C)cccc1C]
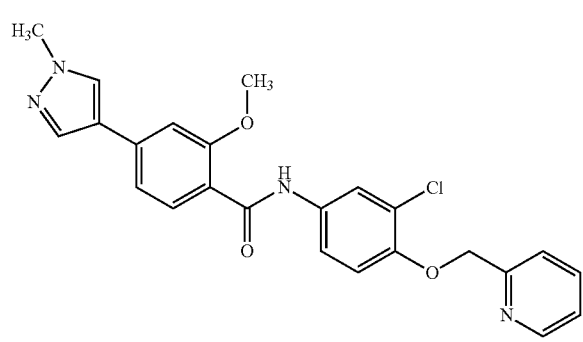 [SMILES: COc1cc(-c2cnn(C)c2)ccc1C(=O)Nc1ccc(OCc2ccccn2)c(Cl)c1]
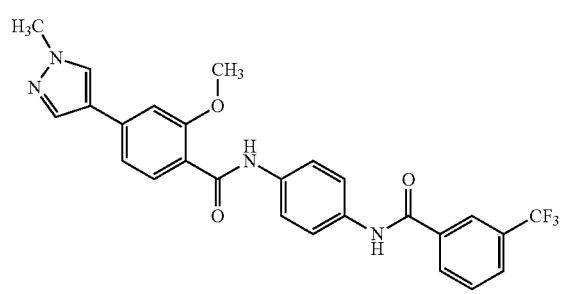 [SMILES: COc1cc(-c2cnn(C)c2)ccc1C(=O)Nc1ccc(NC(=O)c2cccc(C(F)(F)F)c2)cc1]
-continued
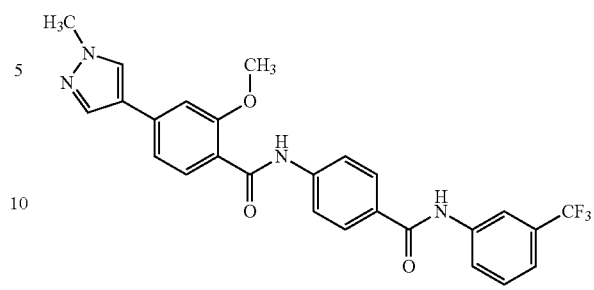
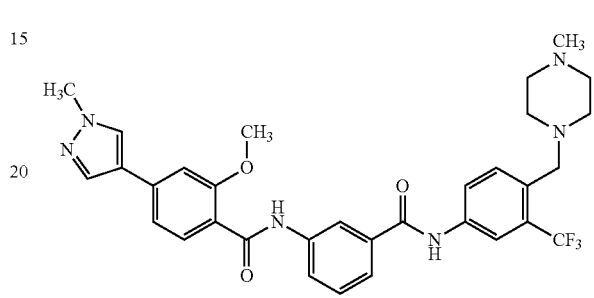
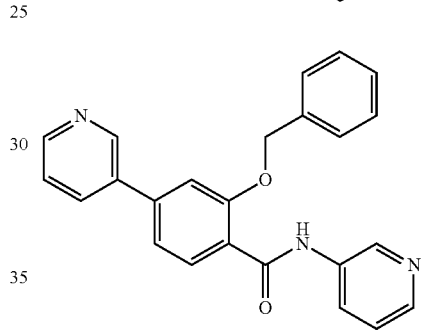
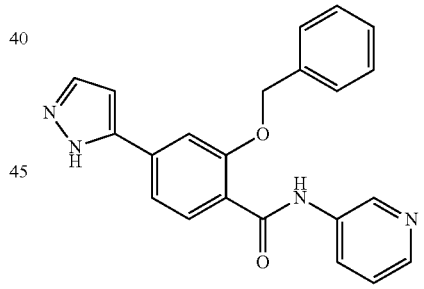
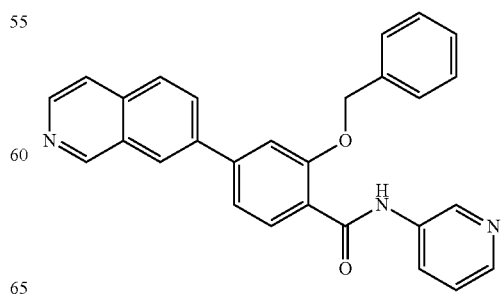

-continued
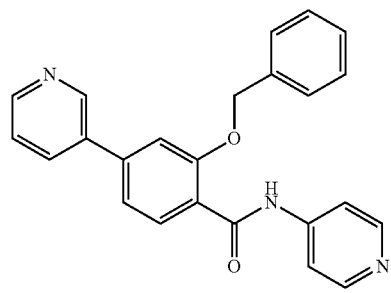 [SMILES: O=C(Nc1ccncc1)c1ccc(-c2cccnc2)cc1OCc1ccccc1]
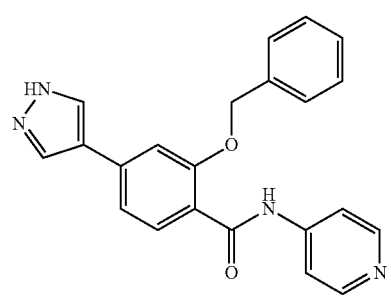 [SMILES: O=C(Nc1ccncc1)c1ccc(-c2cn[nH]c2)cc1OCc1ccccc1]
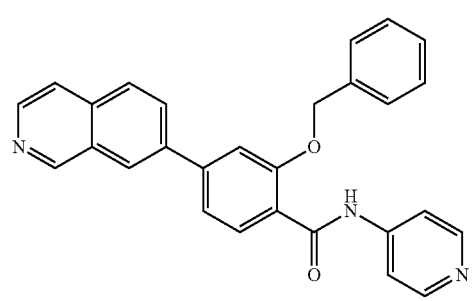 [SMILES: O=C(Nc1ccncc1)c1ccc(-c2ccc3ccncc3c2)cc1OCc1ccccc1]
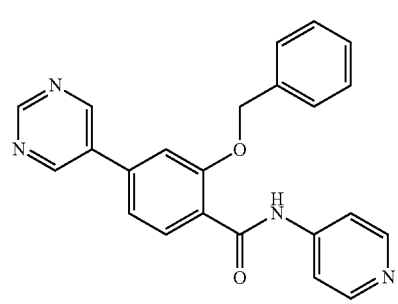 [SMILES: O=C(Nc1ccncc1)c1ccc(-c2cncnc2)cc1OCc1ccccc1]
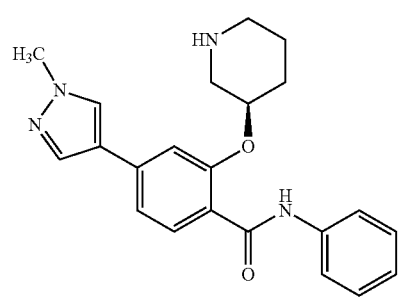 [SMILES: Cn1cc(-c2ccc(C(=O)Nc3ccccc3)c(O[C@@H]3CCCNC3)c2)cn1]
-continued
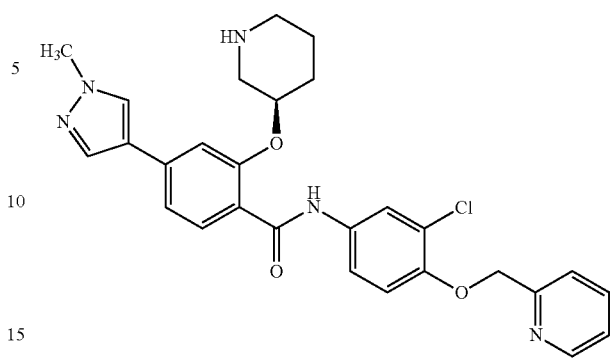
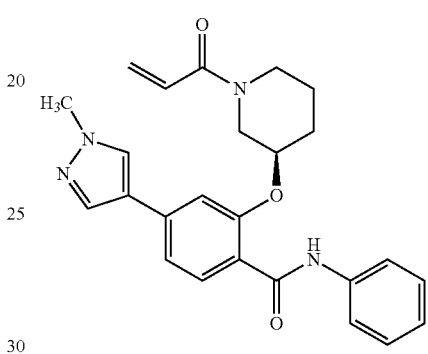
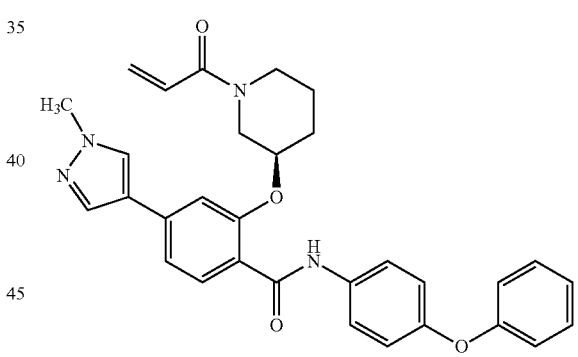
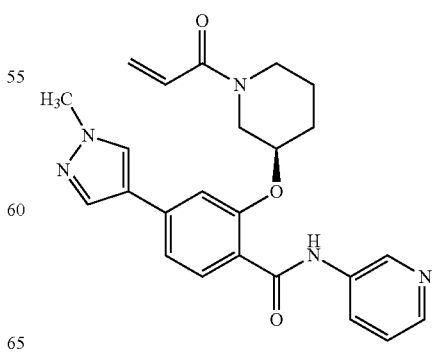

In certain embodiments, the invention provides a compound according to the following table:

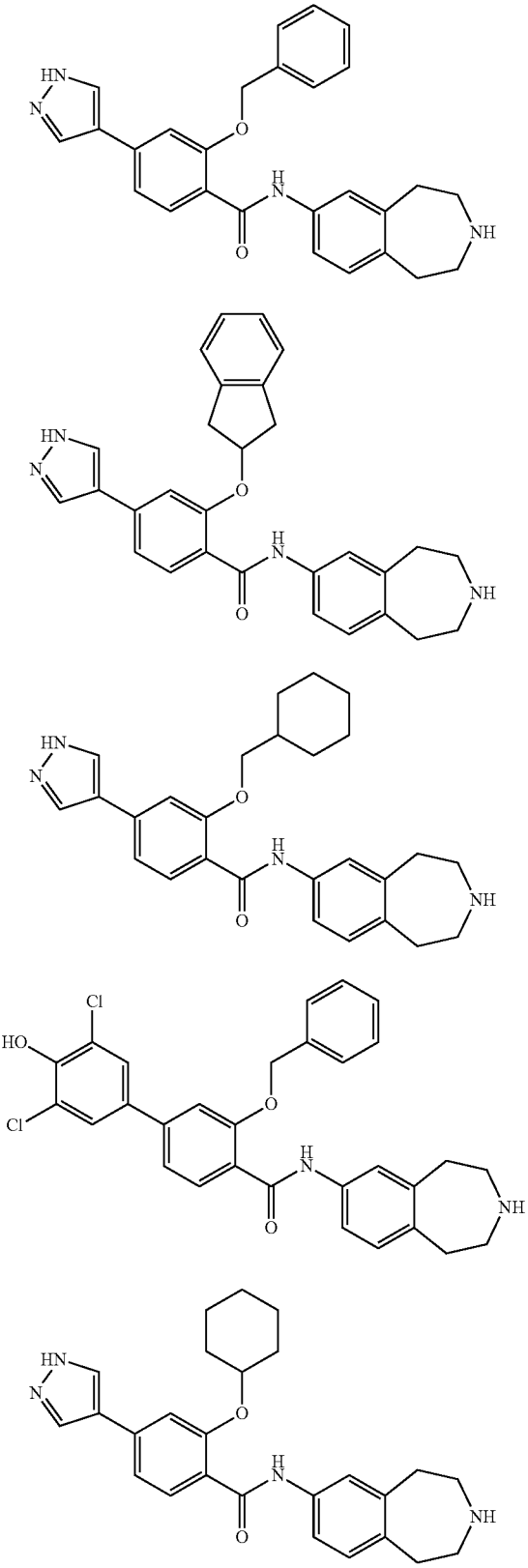

III Pharmaceutical Compositions of the Compounds of the Invention

In certain embodiments, the invention also provides pharmaceutical compositions, comprising a compound of the invention and a pharmaceutically acceptable carrier.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs.

In certain embodiments, the composition is a form suitable for injection, systemic administration, or topical administration. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch.

The composition can also be present in a solution or suspension suitable for topical administration. The topically applicable form of the composition can a transdermal patch, ointment, cream, gel, suspension, liquid, elixir, or eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients.

The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use.

These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for administration to the mouth may be presented as a mouthwash, or an oral spray, or an oral ointment.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations which are suitable for vaginal administration also include pessaries, tampons, creams, gels, pastes, foams or spray formulations containing such carriers as are known in the art to be appropriate.

Alternatively or additionally, compositions can be formulated for delivery via a catheter, stent, wire, or other intraluminal device. Delivery via such devices may be especially useful for delivery to the bladder, urethra, ureter, rectum, or intestine.

Dosage forms for the topical administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

IV Methods of Using the Compounds of the Invention

In certain embodiments, the invention provides methods of treating cancer, comprising administering to a patient in need thereof a therapeutically effective amount of a compound of the invention that is described herein.

In certain embodiments, the cancer is associated with overexpression of MELK. For example, cancer cells or tissues may have a higher or significantly higher expression level of MELK as compared to the expression level in normal cells or tissues. MELK expression can be determined through methods known to those of skill in the art, and such methods include microarray analysis of RNA samples prepared from normal and cancerous tissues.

The "normal" level of expression of a marker (e.g., MELK) is the level of expression of the marker in cells of a subject, e.g., a human patient, not afflicted with a cancer. An "over-expression" or "significantly higher level of expression" of a marker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the marker in a control sample (e.g., sample from a healthy subject not having the marker associated disease) and preferably, the average expression level of the marker in several control samples. A "significantly lower level of expression" of a marker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a healthy subject not having the marker associated disease) and preferably, the average expression level of the marker in several control samples.

In certain embodiments, the invention relates to a method of treating a cancer selected from cervical cancer, colon cancer, breast cancer, gastric cancer, head and neck cancer, leukemia, lung cancer, ovarian cancer, pancreatic cancer, prostate cancer, and brain cancer. In certain embodiments, the cancer is breast cancer, ovarian cancer, or melanoma. In certain embodiments, the invention relates to treating basal-like breast cancer (BBC) with a compound of the invention.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

The term "administering" is intended to include routes of administration which allow the agent to perform its intended function of inhibiting the activity of MELK. Examples of routes of administration which can be used include injection (subcutaneous, intravenous, parenterally, intraperitoneally, intrathecal, etc.), oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. The agent also may be administered as a prodrug, which is converted to its active form in vivo.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, the methods of the invention further comprise conjointly administering to the patient a therapeutically effective amount of a second chemotherapeutic agent.

As used herein, the phrase "conjoint administration" refers to any form of administration of two or more different therapeutic compounds such that the second compound is administered while the previously administered therapeutic compound is still effective in the body (e.g., the two compounds are simultaneously effective in the patient). For example, the different therapeutic compounds can be administered either in the same formulation or in a separate formulation. The different therapeutic compounds, when administered in separate formulations, can be administered either concomitantly (i.e., simultaneously) or sequentially. In certain embodiments, the different therapeutic compounds can be administered within 5 minutes, 30 minutes, one hour, 12 hours, 24 hours, 36 hours, 48 hours, 72 hours, or 168 hours (one week) of one another. Thus, an individual who receives such treatment can benefit from a combined effect of different therapeutic compounds.

In certain embodiments, conjoint administration of compounds of the invention with one or more additional therapeutic agents (e.g., one or more additional chemotherapeutic agents) provides improved efficacy relative to each individual administration of the compound of the invention (e.g., a compound of Formula (I)) or the one or more additional therapeutic agents. In certain such embodiments, the conjoint administration provides an additive effect, wherein an additive effect refers to the sum of each of the effects of individual administration of the compound of the invention and the one or more additional therapeutic agents.

In certain embodiments, conjoint administration of compounds of the invention with one or more additional therapeutic agents (e.g., one or more additional chemotherapeutic agents) provides improved efficacy relative to the sum of each of the effects of individual administration of the compound of the invention and the one or more additional therapeutic agents (i.e., relative to the additive effect). In certain such embodiments, conjoint administration of the compound of the invention and the second chemotherapeutic agent provides a synergistic effect. In certain embodiments, the second chemotherapeutic agent is paclitaxel.

In certain embodiments, the methods of the invention further comprise conjointly administering to the patient radiation therapy.

The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (1-125, Pd-103, Ir-192), intravenous administration of radioisotopes such as strontium-89, thoracic radiation therapy, intraperitoneal $^{32}$P radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In certain embodiments, the methods of the invention further comprise conjointly administering to the patient an additional anti-cancer agent such as immunotherapy, hormone therapy, and gene therapy. Such therapies include, but are not limited to, the use of antisense polynucleotides, ribozymes, RNA interference molecules, triple helix polynucleotides and the like, where the nucleotide sequence of such compounds are related to the nucleotide sequences of DNA and/or RNA of genes that are linked to the initiation, progression, and/or pathology of a tumor or cancer. For example, oncogenes, growth factor genes, growth factor receptor genes, cell cycle genes, DNA repair genes, and others, may be targeted in such therapies.

Immunotherapy may comprise, for example, use of cancer vaccines and/or sensitized antigen presenting cells. Immunotherapy can also involve derepression of immunoinhibitory pathways, such as by targeting PD-L1, PD-L2, PD-1, CTLA-4, and the like. The immunotherapy can involve passive immunity for short-term protection of a host, achieved by the administration of an antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines.

Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

The invention also provides methods for inhibiting MELK, comprising contacting MELK with a compound of the invention in an amount effective to inhibit MELK. In certain embodiments, the method is conducted in vitro. In certain embodiments, the method is conducted in vivo. Inhibition of MELK can be determined by the Z'-LYTE® biochemical assay from Life Technologies (Life Technologies Z'-LYTE® Screening Protocol and Assay Conditions, June 2012, incorporated herein by reference).

The invention also provides methods for treating or preventing a condition associated with aberrant maternal embryonic leucine zipper kinase (MELK), comprising administering to a subject in need thereof a therapeutically effective amount of a compound of the invention.

In certain embodiments, the invention provides methods for treating or preventing a condition associated with hyperactivation of MELK, or a condition associated with an essential role of MELK in disease progression and/or maintenance.

In certain embodiments, the condition to be treated is associated with heightened expression of MELK. In certain embodiments, the condition to be treated is associated with heightened activity of MELK.

The invention also provides methods for decreasing the rate of mitosis in a cancer cell, comprising contacting a cancer cell a compound of the invention in an amount effective to decrease the rate of mitosis of the cancer cell. The rate of mitosis of cancer cells can be measured through methods known to persons of skill in the art. These methods include immunohistochemical analysis of established mitotic markers, such as Histone H3 phosphorylation.

In addition to the assessing the rate of mitosis of a cancer cell after treatment with a compound of the invention, the response to cancer therapy can be assessed. The term "response to cancer therapy" or "outcome of cancer therapy" relates to any response of the hyperproliferative disorder (e.g., cancer) to a cancer therapy, preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Response may also be assessed by caliper measurement or pathological examination of the tumor after biopsy or surgical resection for solid cancers. Responses may be recorded in a quantitative fashion like percentage change in tumor volume. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to copy number, level of expression, level of activity, etc. of a marker (e.g., MELK) determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom the measurement values are known. In certain embodiments, the same doses of cancer therapeutic agents are administered to each subject. In related embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Outcomes can also be measured in terms of a "hazard ratio" (the ratio of death rates for one patient group to another; provides likelihood of death at a certain time point), "overall survival" (OS), and/or "progression free survival." In certain embodiments, the prognosis comprises likelihood of overall survival rate at 1 year, 2 years, 3 years, 4 years, or any other suitable time point. The significance associated with the prognosis of poor outcome in all aspects of the present invention is measured by techniques known in the art. For example, significance may be measured with calculation of odds ratio. In a further embodiment, the significance is measured by a percentage. In one embodiment, a significant risk of poor outcome is measured as odds ratio of 0.8 or less or at least about 1.2, including by not limited to: 0.1, 0.2, 0.3, 0.4, 0.5, 0.6, 0.7, 0.8, 1.2, 1.3, 1.4, 1.5, 1.6, 1.7, 1.8, 1.9, 2.0, 2.5, 3.0, 4.0, 5.0, 10.0, 15.0, 20.0, 25.0, 30.0 and 40.0. In a further embodiment, a significant increase or reduction in risk is at least about 20%, including but not limited to about 25%, 30%, 35%, 40%, 45%, 50%, 55%, 60%, 65%, 70%, 75%, 80%, 85%, 90%, 95% and 98%. In a further embodiment, a significant increase in risk is at least about 50%.

EXAMPLES

Example 1

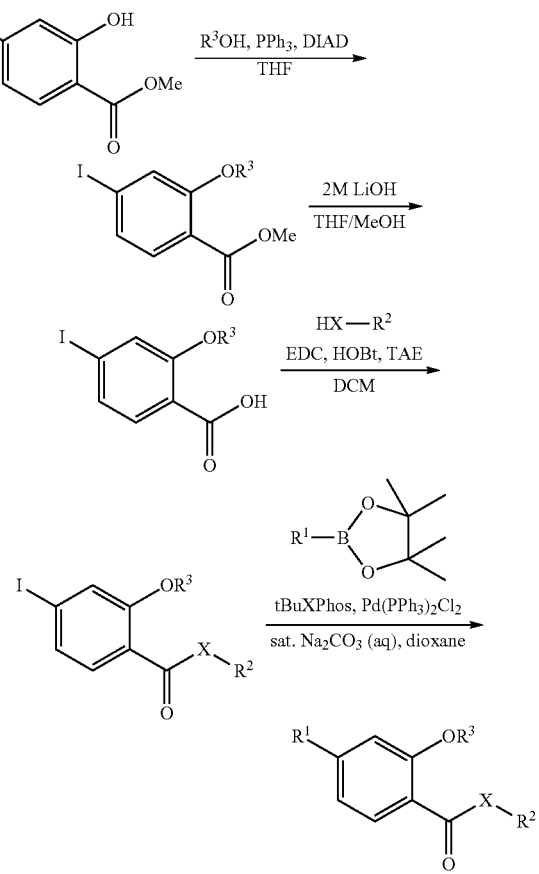

Scheme 1. General Synthetic Scheme for Formula (I).

Numerous compounds of the invention were made according to Scheme 1. Additional steps such as functional group manipulations, protections, and deprotections are contemplated and are within the skills and knowledge of a person of ordinary skill in the art. The following examples provide exemplary synthetic protocols for making the compounds of the invention.

Example 2

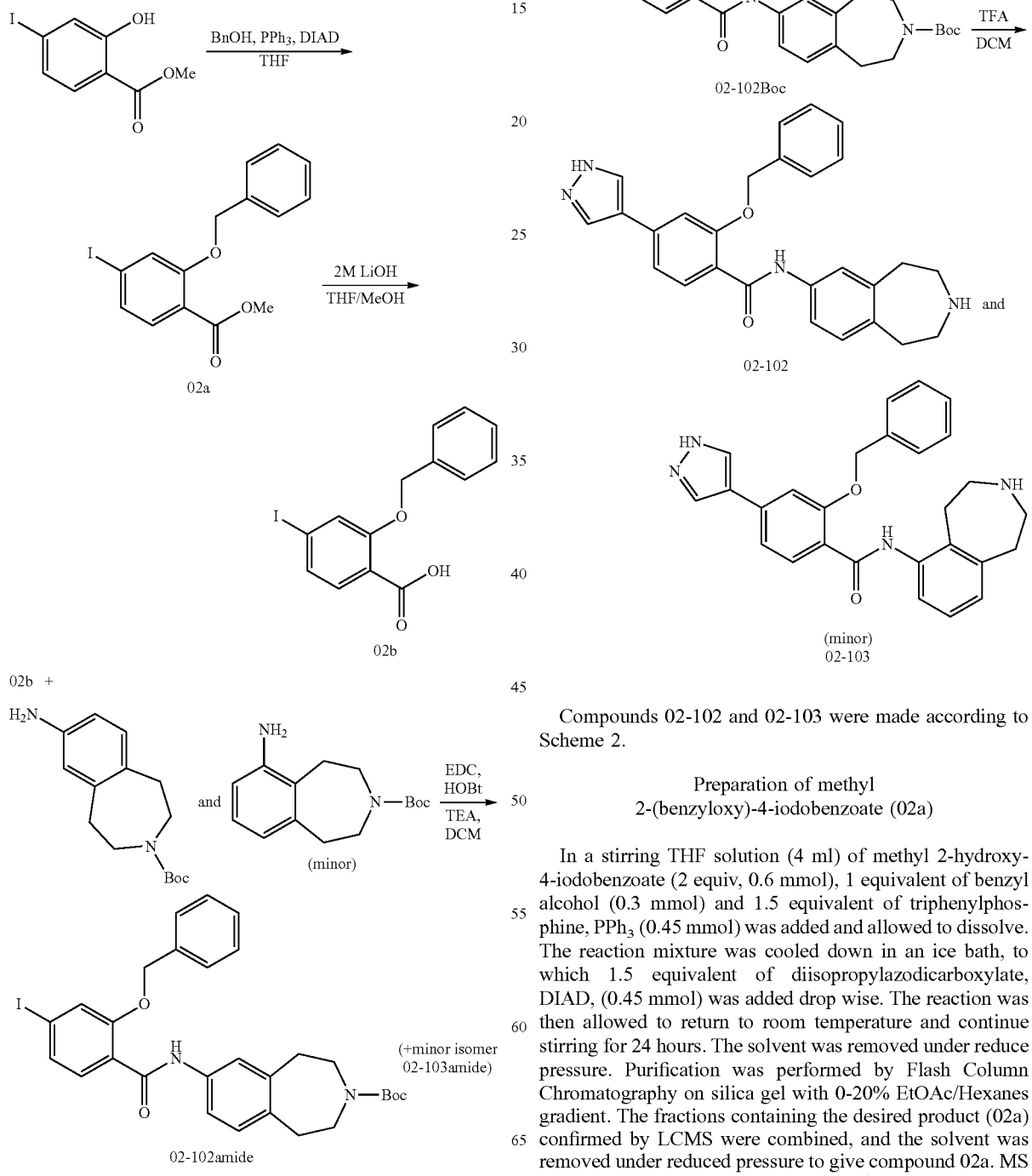

Compounds 02-102 and 02-103 were made according to Scheme 2.

Preparation of methyl 2-(benzyloxy)-4-iodobenzoate (02a)

In a stirring THF solution (4 ml) of methyl 2-hydroxy-4-iodobenzoate (2 equiv, 0.6 mmol), 1 equivalent of benzyl alcohol (0.3 mmol) and 1.5 equivalent of triphenylphosphine, PPh$_3$ (0.45 mmol) was added and allowed to dissolve. The reaction mixture was cooled down in an ice bath, to which 1.5 equivalent of diisopropylazodicarboxylate, DIAD, (0.45 mmol) was added drop wise. The reaction was then allowed to return to room temperature and continue stirring for 24 hours. The solvent was removed under reduce pressure. Purification was performed by Flash Column Chromatography on silica gel with 0-20% EtOAc/Hexanes gradient. The fractions containing the desired product (02a) confirmed by LCMS were combined, and the solvent was removed under reduced pressure to give compound 02a. MS (ESI) calculated for $C_{15}H_{14}IO_3$ [M+H]$^+$, 369; found 369.

Preparation of tert-butyl 7-(2-(benzyloxy)-4-iodo-
benzamido)-1,2,4,5-tetrahydro-3H-benzo[d]azepine-
3-carboxylate (02-102a) and tert-butyl 6-(2-(benzy-
loxy)-4-iodobenzamido)-1,2,4,5-tetrahydro-3H-
benzo[d]azepine-3-carboxylate (02-103a)

In a stirring THF/MeOH(1:1) solution (1 mL) of 2-(ben-zyloxy)-4-iodobenzoate (02a) (0.5 mmol), equal volume of 2N LiOH(aq) was added. The reaction was allowed to stir for 24 hours at room temperature. The reaction mixture was neutralized with 1N HCl(aq) (2 mL) and 10 mL of water was added. The organic layer was extracted with CHCl$_3$:iPrOH (4:1) (15 mL×3) and washed with brine solution (10 mL). The organic layer was further dried with MgSO$_4$, filtered, and the solvent was removed under reduced pressure. The product (02b) was directly used for the next step without purification.

In a stirring CH$_2$Cl$_2$ solution (2 mL) of 1.2 equivalent of 02b (0.19 mmol), 1.0 equivalent of tert-butyl 7-amino-1,2,4,5-tetrahydro-3H-benzo[d]azepine-3-carboxylate (0.16 mmol), 2.0 equivalent of triethylamine (0.320 mmol), and 1.4 equivalent of hydroxybenzotriazole, HOBt (0.223 mmol), were added, and allowed to dissolve. To the reaction mixture was added 1.4 equivalent of N-(3-dimethylamino-propyl)-N'-ethylcarbodiimide hydrochloride, EDC*HCl (0.223 mmol), and continue stirring overnight at room temperature. The reaction was worked up in 1N NaOH(aq) (10 mL) and dichloromethane (10 mL×3). The organic layers were collected and washed with brine solution (10 mL). Purification was performed by Flash Column Chromatography on silica gel with 0-20% CH$_2$Cl$_2$/methanol (1.75N ammonia) gradient. The fractions containing the desired product (02-102amide) were combined with the minor isomer was still present, and the solvent was removed under reduced pressure. MS(ESI) calculated for C$_{25}$H$_{24}$IN$_2$O$_4$[M+H−56]+, 543; found 543.

Preparation of 2-(benzyloxy)-4-(1H-pyrazol-4-yl)-
N-(2,3,4,5-tetrahydro-1H-benzo[d]azepin-7-yl)benz-
amide (02-102)

In a dioxane/sat. Na$_2$CO$_3$(aq)(3:1) solution (0.8 mL) containing 1 equivalent of 02-102amide (0.05 mmol), 1.5 equivalent of tert-butyl 4-(4,4,5,5-tetramethyl-1,3,2-dioxa-borolan-2-yl)-1H-pyrazole-1-carboxylate (0.075 mmol), and 10% equivalent of 2-di-tert-butylphosphino-2',4',6'-tri-isopropylbiphenyl (0.005 mmol) were added. The reaction was purged thoroughly with argon, to which 10% equivalent of bis(tripheylphosphine)palladium(II) dichloride (0.005 mmol) was added. The reaction was heated to 80° C. and continue stirring overnight. The reaction was worked up in water (10 mL) and CHCl$_3$:iPrOH(4:1) (15 mL×3). The organic layers were collected and washed with brine solution (10 mL). Purification was performed by reverse-phase prep-HPLC (C18) using water (0.05% trifluoroacetic acid)/methanol (0.05% trifluoroacetic acid) gradient to afford 02-102Boc, free of the minor isomer 02-103Boc. The compound 02-102Boc was briefly treated with 10% trifluoroacetic acid in dichloromethane to remove the Boc protecting group. Purification was performed by Flash Column Chromatography on silica gel with 0-20% CH$_2$Cl$_2$/methanol (1.75N ammonia) gradient. The fractions containing the desired product (02-102) confirmed by LCMS were combined, and the solvent was removed under reduced pressure to afford the product as a free base: $^1$H NMR (400 MHz, DMSO-d$_6$) δ 13.08 (br s, 1H); 9.97 (s, 1H); 8.23 (br s, 2H); 7.82 (d, J=7.8 Hz, 1H); 7.64 (dd, J=7.8, 1.6 Hz, 2H); 7.56 (d, J=1.2 Hz, 1H); 7.48-7.41 (m, 3H); 7.38 (dd, J=7.8, 1.2 Hz, 1H); 7.29 (dd, J=7.8, 2.0 Hz, 1H); 6.98 (d, J=8.2 Hz, 1H); 6.91 (d, J=2.0 Hz, 1H); 5.36 (s, 2H); 2.81-2.69 (m, 8H). MS (ESI) calculated for C$_{27}$H$_{27}$N$_4$O$_2$ [M+H]$^+$, 438.521; found 439.

MELK IC$_{50}$ as determined by Z'-LYTE® biochemical assay: 2.17 nM.

Compound 02-103. Calculated mass: 438.521. Observed mass: 439. MELK IC$_{50}$ as determined by Z'-LYTE® biochemical assay: 134 nM.

Example 3

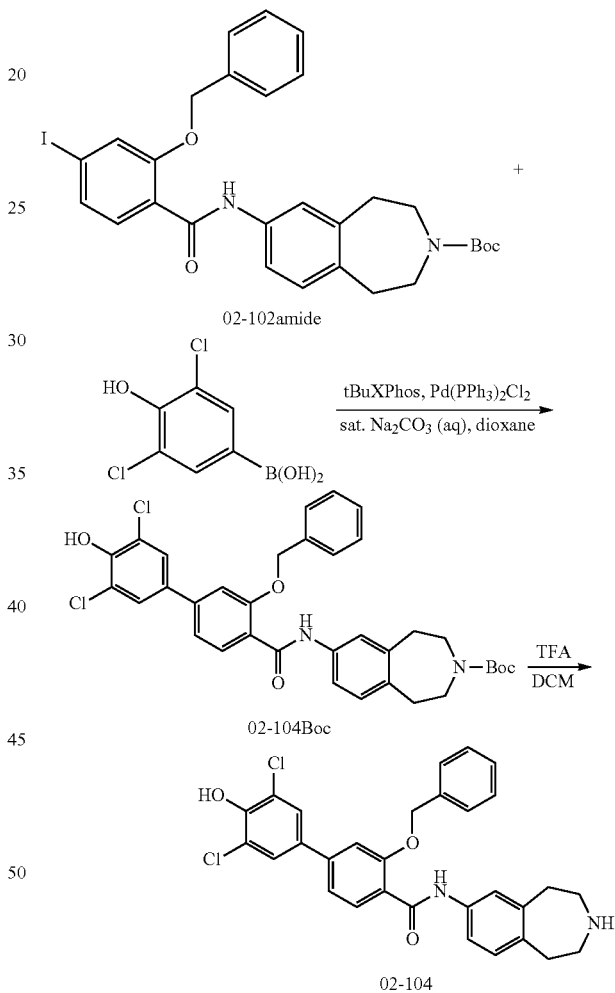

Preparation of 3-(benzyloxy)-3',5'-dichloro-4'-hy-
droxy-N-(2,3,4,5-tetrahydro-1H-benzo[d]azepin-7-
yl)-[1,1'-biphenyl]-4-carboxamide (02-104)

In a dioxane/sat. Na$_2$CO$_3$(aq)(3:1) solution (0.8 mL) containing 1 equivalent of 02-102amide (0.043 mmol), 1.5 equivalent of (3,5-dichloro-4-hydroxyphenyl)boronic acid (0.064 mmol), and 10% equivalent of 2-di-tert-butylphosphino-2',4',6'-triisopropylbiphenyl (0.004 mmol) was added. The reaction was purged thoroughly with argon, to which 10% equivalent of bis(tripheylphosphine)palladium(II) dichloride (0.004 mmol) was added. The reaction was heated to 80° C. and continue stirring overnight. The reaction was worked up in water (10 mL) and CHCl$_3$:iPrOH(4:1) (15 mL×3). The organic layers were collected and washed with brine solution (10 mL). Purification was performed by reverse-phase prep-HPLC (C18) using water (0.05% trifluoroacetic acid)/methanol (0.05% trifluoroacetic acid) gradient to afford 02-104Boc. Then, 02-104Boc was treated with 10% trifluoroacetic acid in dichloromethane to remove the Boc protecting group. Purification was performed by reverse-phase prep-HPLC (C18) using water (0.05% trifluoroacetic acid)/methanol (0.05% trifluoroacetic acid) gradient to afford the compound 02-104 as a trifluoroacetic salt: $^1$H NMR (400 MHz, DMSO-d$_6$) δ 10.13 (s, 1H); 7.85 (s, 2H); 7.80 (d, J=8.2 Hz, 1H); 7.63-7.57 (m, 3H); 7.46-7.37 (m, 4H); 7.33 (dd, J=8.2, 2.0 Hz, 1H); 7.25 (d, J=2.0 Hz, 1H); 7.12 (d, J=8.2 Hz, 1H); 5.41 (s, 2H); 3.22-3.13 (m, 4H); 3.04-2.93 (m, 4H). MS (ESI) calculated for C$_{30}$H$_{27}$Cl$_2$N$_2$O$_3$ [M+H]$^+$, 532.132; found 533.

MELK IC$_{50}$ as determined by Z'-LYTE® biochemical assay: 1.92 nM.

Example 4

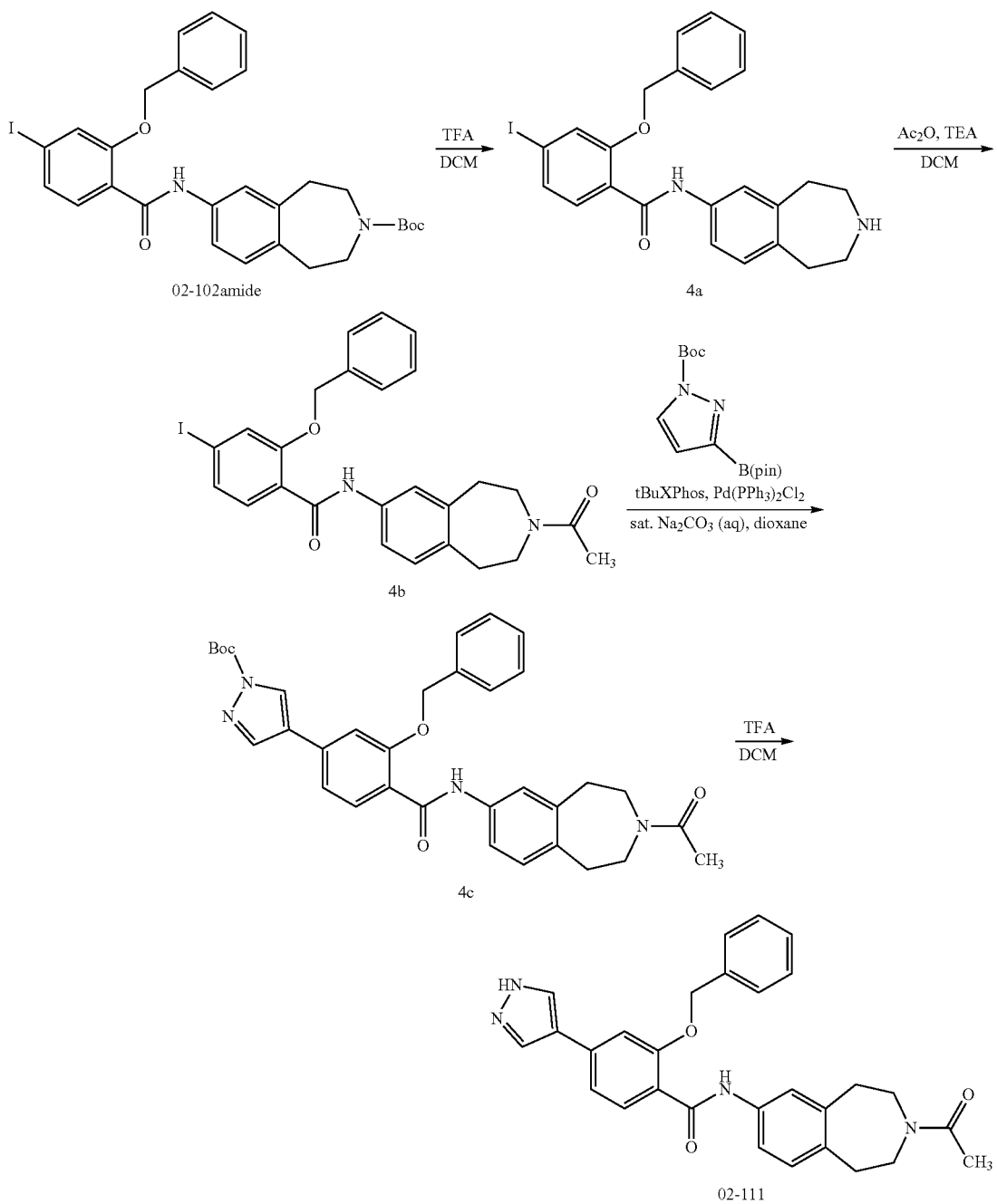

Preparation of N-(3-acetyl-2,3,4,5-tetrahydro-1H-benzo[d]azepin-7-yl)-2-(benzyloxy)-4-iodobenzamide (4b)

In a stirring CH$_2$Cl$_2$ solution (1 mL) containing 02-102amide (0.064 mmol), 0.5 mL of trifluoroactic acid was added. The reaction was allowed to stir for 1 hour at room temperature. The solvent was removed under reduced pressure. The crude product (4a) was directly used for the next step without purification.

In a stirring CH$_2$Cl$_2$ solution (1 mL) of 1.0 equivalent of 4a (0.064 mmol), 1.2 equivalent of acetic anhydride, and 10.0 equivalent of triethylamine (0.64 mmol) were added, and continue stirring for 3 hours at room temperature. The reaction was worked up in 1N NaOH(aq) (10 mL) and dichloromethane (10 mL×3). The organic layers were collected and washed with brine solution (10 mL). Purification was performed by reverse-phase prep-HPLC (C18) using water (0.05% trifluoroacetic acid)/methanol (0.05% trifluoroacetic acid) gradient to afford the compound 4b. MS(ESI) calculated for C$_{26}$H$_{26}$IN$_2$O$_3$[M+H]$^+$, 541; found 541.

Preparation of N-(3-acetyl-2,3,4,5-tetrahydro-1H-benzo[d]azepin-7-yl)-2-(benzyloxy)-4-(1H-pyrazol-4-yl)benzamide (02-111)

In a dioxane/sat. Na$_2$CO$_3$(aq)(3:1) solution (0.8 mL) containing 1 equivalent of 4b (0.022 mmol), 1.5 equivalent of tert-butyl 4-(4,4,5,5-tetramethyl-1,3,2-dioxaborolan-2-yl)-1H-pyrazole-1-carboxylate (0.033 mmol), and 10% equivalent of 2-di-tert-butylphosphino-2',4',6'-triisopropylbiphenyl (0.002 mmol) was added. The reaction was purged thoroughly with argon, to which 10% equivalent of bis(tripheylphosphine)palladium(II) dichloride (0.002 mmol) was added. The reaction was heated to 80° C. and continue stirring overnight. The reaction was worked up in water (10 mL) and CHCl$_3$:iPrOH(4:1) (15 mL×3). The organic layers were collected and washed with brine solution (10 mL). Purification was performed by reverse-phase prep-HPLC (C18) using water (0.05% trifluoroacetic acid)/methanol (0.05% trifluoroacetic acid) gradient to afford the compound 4c. The compound 4c was briefly treated with 10% trifluoroacetic acid in dichloromethane to remove the Boc protecting group. Purification was performed by Flash Column Chromatography on silica gel with 0-10% CH$_2$Cl$_2$/methanol (1.75N ammonia) gradient. The fractions containing the desired product 02-111 confirmed by LCMS were combined, and the solvent was removed under reduced pressure to afford the product as a free base: $^1$H NMR (400 MHz, DMSO-d$_6$) δ 13.07 (br s, 1H); 10.01 (s, 1H); 8.38 (br s, 1H); 8.09 (br s, 1H); 7.82 (dd, J=8.2, 1.2 Hz, 1H); 7.64 (dd, J=8.2, 2.0 Hz, 2H); 7.57 (d, J=1.2 Hz, 1H); 7.49-7.43 (m, 3H); 7.38 (dd, J=8.2, 1.2 Hz, 1H); 7.34 (ddd, J=14.9, 7.8, 2.0 Hz, 1H); 7.05 (dd, J=7.8, 7.8 Hz, 1H); 6.97 (dd, J=25.0, 2.0 Hz, 1H); 5.36 (s, 2H); 3.58-3.47 (m, 4H); 2.87-2.64 (m, 4H); 2.07 (d, J=5.9 Hz, 3H). MS (ESI) calculated for C$_{29}$H$_{29}$N$_4$O$_3$ [M+H]$^+$, 480.216; found 481.

MELK IC$_{50}$ as determined by Z'-LYTE® biochemical assay: 60.6 nM.

Example 5

The following compounds were made according to the general scheme shown in Example 1. IC$_{50}$ against MELK was determined by Z'-LYTE® biochemical assay at 25 uM ATP concentration, and are measured in nM.

Compound 02-112

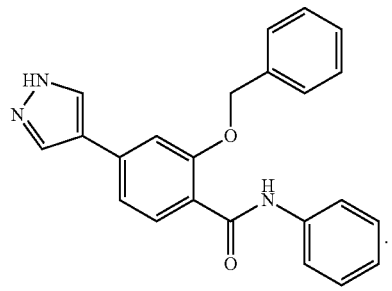

Calculated mass: 369.148. Observed mass: 370. MELK IC$_{50}$: 1160.

Compound 02-119

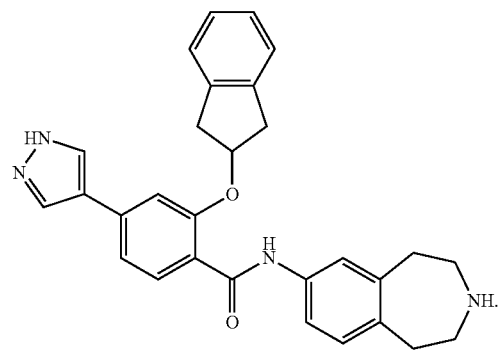

Calculated mass: 464.221. Observed mass: 465. MELK IC$_{50}$: 1.05.

Compound 02-123

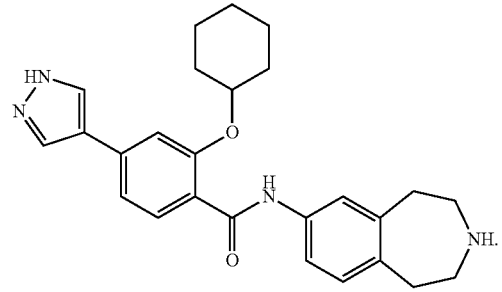

Calculated mass: 430.237. Observed mass: 431. MELK IC$_{50}$: 2.99.

Compound 02-124

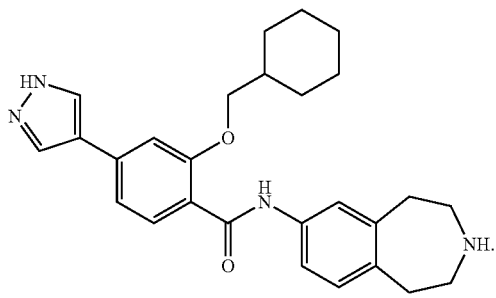

Calculated mass: 444.253. Observed mass: 445. MELK IC$_{50}$: 5.48.

Compound 02-125

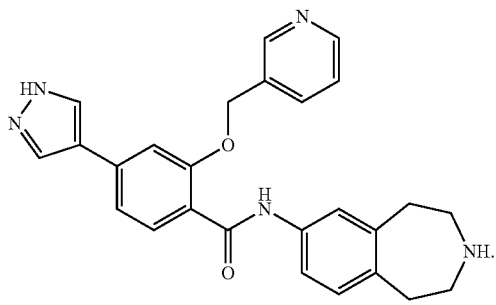

Calculated mass: 439.201. Observed mass: 440. MELK IC$_{50}$: 16.2.

Compound 02-138

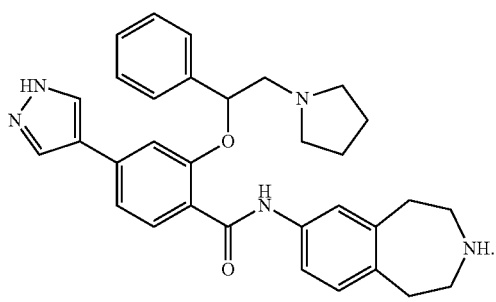

Calculated mass: 521.279. Observed mass: 522. MELK IC$_{50}$: 213.

Compound 02-139

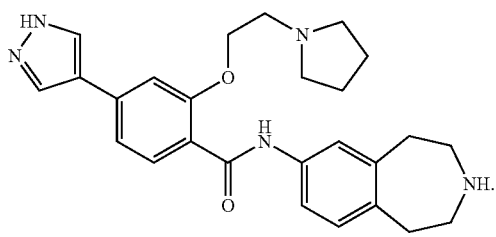

Calculated mass: 445.248. Observed mass: 446. MELK IC$_{50}$: 75.1.

Compound 02-140

Calculated mass: 459.227. Observed mass: 460. MELK IC$_{50}$: 80.6.

Compound 02-143

Calculated mass: 461.243. Observed mass: 462. MELK IC$_{50}$: 85.3.

Compound 02-144

Calculated mass: 348.159. Observed mass: 349. MELK IC$_{50}$: 68.8.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A compound represented by formula (I) or a pharmaceutically acceptable salt thereof:

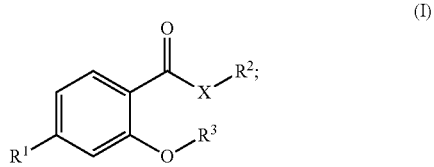

wherein:
- R¹ represents substituted or unsubstituted pyrrolyl, pyrazolyl, indazolyl, indolyl, isoquinolinyl, pyrimidinyl, isoxazolyl, oxazolyl, pyridazinyl, pyrazinyl, benzimidazolyl, benzimidazolonyl, benzothiazolonyl, quinolinyl, quinzolinyl, or quinoxalinyl;
- R² represents substituted or unsubstituted aryl, heteroaryl, aralkyl, or heteroaralkyl;
- R³ represents substituted or unsubstituted alkyl, cycloalkyl, (cycloalkyl)alkyl, aralkyl, heteroarylalkyl, heterocycloalkyl, or (heterocycloalkyl)alkyl, wherein the substituted or unsubstituted alkyl comprises a tertiary or quaternary carbon; and
- X represents NH;
- provided that when R² represents substituted or unsubstituted aryl, then R³ is not aralkyl.

2. The compound of claim 1, wherein R³ represents substituted or unsubstituted cycloalkyl, (cycloalkyl)alkyl, aralkyl, heteroarylalkyl, heterocycloalkyl, or (heterocycloalkyl)alkyl.

3. The compound of claim 1, wherein R³ is isopropyl, benzyl, cyclohexyl, cyclohexylmethyl, (3-pyridinyl)methyl, or 2,3-dihydro-1H-inden-2-yl.

4. The compound of claim 1, wherein R¹ is optionally substituted by one or more substituents selected from $(C_1$-$C_6)$alkyl, $(C_1$-$C_6)$alkoxy, $(C_1$-$C_6)$haloalkyl, halo, —OH, $(C_1$-$C_6)$haloalkoxyl, —SH, —S$((C_1$-$C_6)$alkyl), $(C_1$-$C_6)$hydroxyalkyl, and —$CF_3$.

5. The compound of claim 1, wherein R² represents substituted or unsubstituted aryl or heteroaryl.

6. The compound of claim 1, wherein R² represents substituted or unsubstituted 2-pyridinyl, 3-pyridinyl, or 4-pyridinyl.

7. The compound of claim 1, wherein R² represents

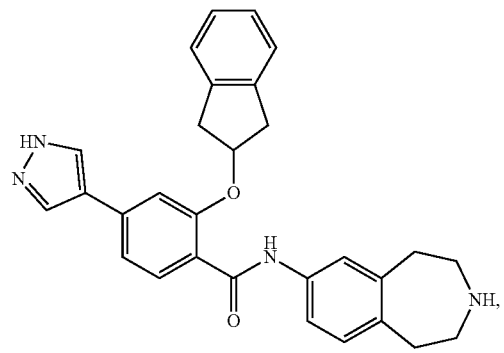

wherein m and n are integers, each independently selected from 0 and 1.

8. The compound of claim 1, wherein R² represents substituted or unsubstituted heteroaryl, aralkyl, or heteroaralkyl.

9. The compound of claim 1, wherein R³ represents substituted or unsubstituted cycloalkyl, (cycloalkyl)alkyl, heteroarylalkyl, heterocycloalkyl, or (heterocycloalkyl)alkyl.

10. The compound of claim 1, wherein R² represents substituted or unsubstituted heteroaryl, aralkyl, or heteroaralkyl; and R³ represents substituted or unsubstituted cycloalkyl, (cycloalkyl)alkyl, heteroarylalkyl, heterocycloalkyl, or (heterocycloalkyl)alkyl.

11. The compound of claim 1, represented by any of the following structural formulae:

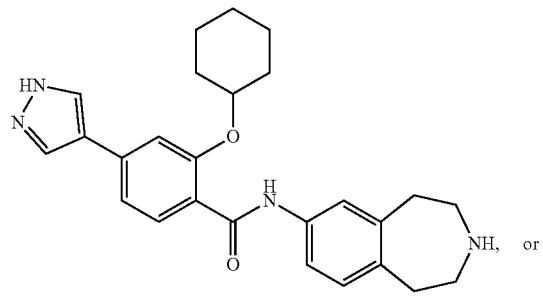

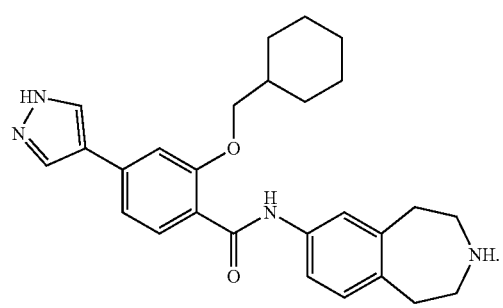 [SMILES: O=C(Nc1ccc2c(c1)CCNCC2)c1ccc(-c2cn[nH]c2)cc1OCC1CCCCC1]

12. A compound, or a pharmaceutically acceptable salt thereof, represented by any of the following structural formulae:

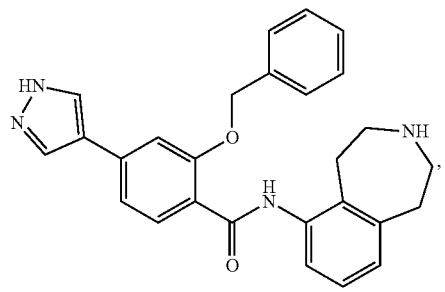 [SMILES: O=C(Nc1cccc2c1CCNCC2)c1ccc(-c2cn[nH]c2)cc1OCc1ccccc1]
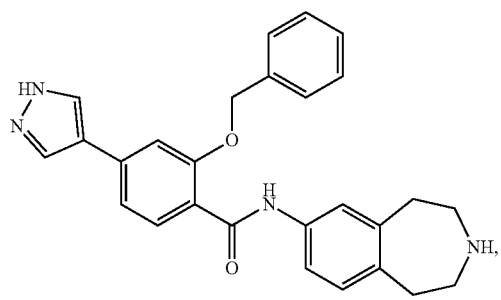 [SMILES: O=C(Nc1ccc2c(c1)CCNCC2)c1ccc(-c2cn[nH]c2)cc1OCc1ccccc1]
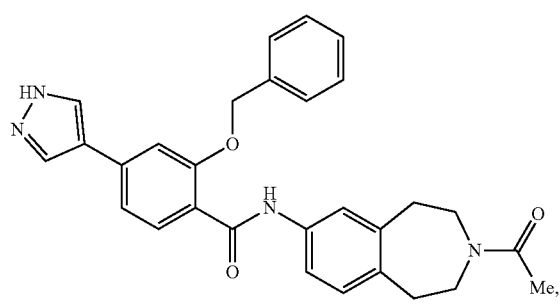 [SMILES: CC(=O)N1CCc2ccc(NC(=O)c3ccc(-c4cn[nH]c4)cc3OCc3ccccc3)cc2CC1]
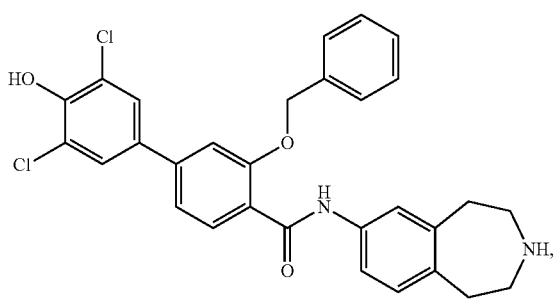 [SMILES: O=C(Nc1ccc2c(c1)CCNCC2)c1ccc(-c2cc(Cl)c(O)c(Cl)c2)cc1OCc1ccccc1]
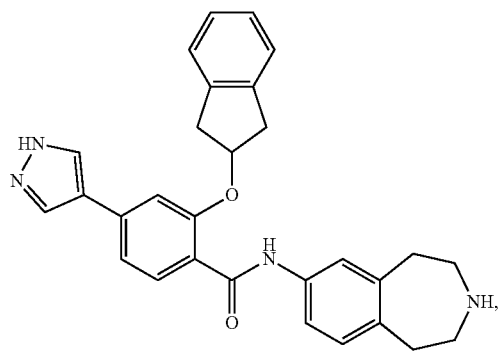 [SMILES: O=C(Nc1ccc2c(c1)CCNCC2)c1ccc(-c2cn[nH]c2)cc1OC1Cc2ccccc2C1]

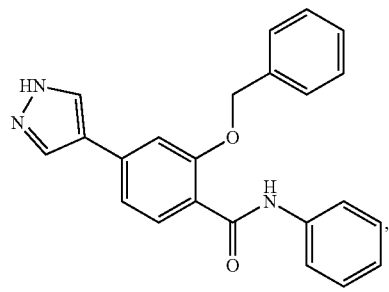 [SMILES: O=C(Nc1ccccc1)c1ccc(-c2cn[nH]c2)cc1OCc1ccccc1]
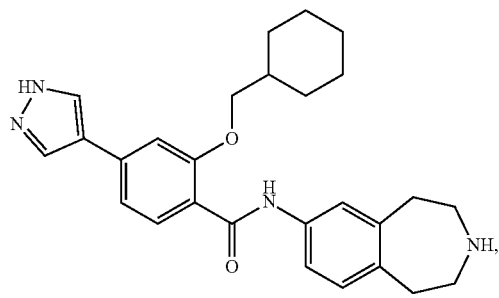 [SMILES: O=C(Nc1ccc2c(c1)CCNCC2)c1ccc(-c2cn[nH]c2)cc1OCC1CCCCC1]
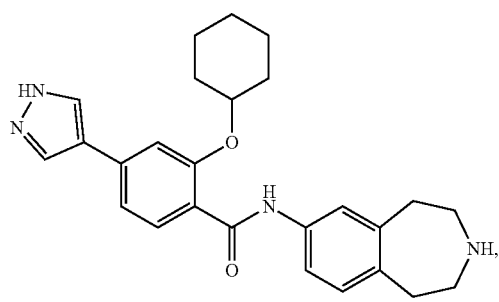 [SMILES: O=C(Nc1ccc2c(c1)CCNCC2)c1ccc(-c2cn[nH]c2)cc1OC1CCCCC1]
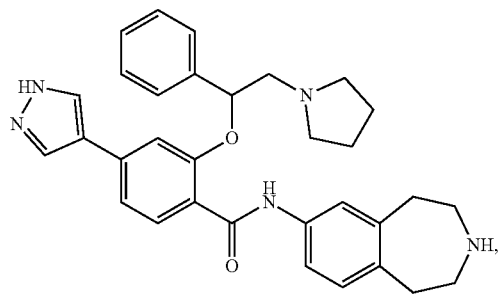 [SMILES: O=C(Nc1ccc2c(c1)CCNCC2)c1ccc(-c2cn[nH]c2)cc1OC(CN1CCCC1)c1ccccc1]
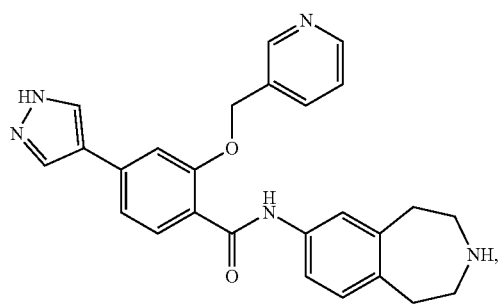 [SMILES: O=C(Nc1ccc2c(c1)CCNCC2)c1ccc(-c2cn[nH]c2)cc1OCc1cccnc1]

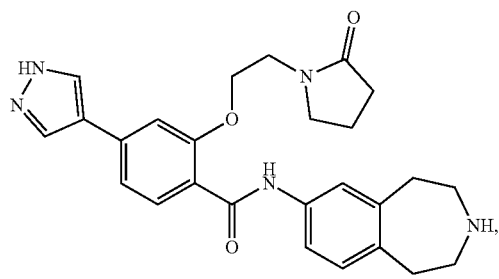 [SMILES: O=C(Nc1ccc2c(c1)CCNCC2)c1ccc(-c2cn[nH]c2)cc1OCCN1CCCC1=O]
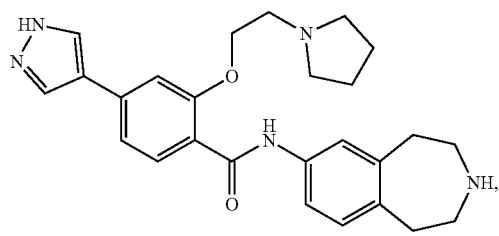 [SMILES: O=C(Nc1ccc2c(c1)CCNCC2)c1ccc(-c2cn[nH]c2)cc1OCCN1CCCC1]
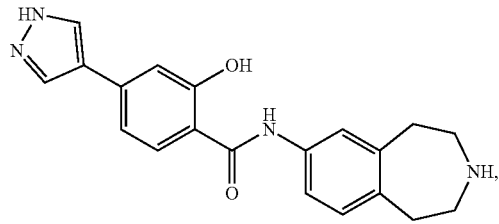 [SMILES: O=C(Nc1ccc2c(c1)CCNCC2)c1ccc(-c2cn[nH]c2)cc1O]
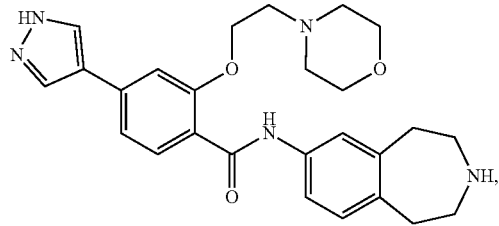 [SMILES: O=C(Nc1ccc2c(c1)CCNCC2)c1ccc(-c2cn[nH]c2)cc1OCCN1CCOCC1]
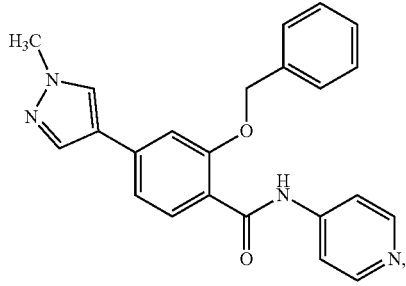 [SMILES: Cn1cc(-c2ccc(C(=O)Nc3ccncc3)c(OCc3ccccc3)c2)cn1]
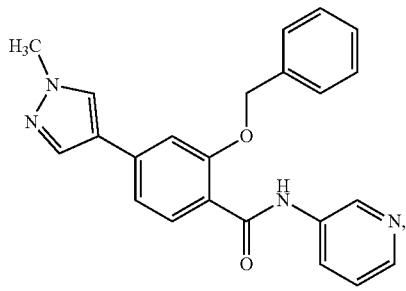 [SMILES: Cn1cc(-c2ccc(C(=O)Nc3cccnc3)c(OCc3ccccc3)c2)cn1]

-continued
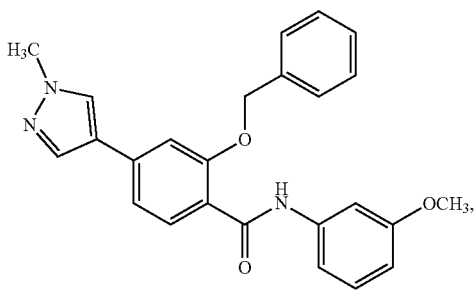 [SMILES: COc1cccc(NC(=O)c2ccc(-c3cnn(C)c3)cc2OCc2ccccc2)c1]
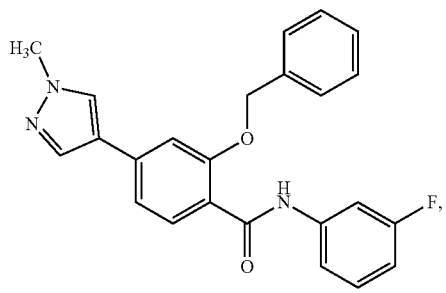 [SMILES: Cn1cc(-c2ccc(C(=O)Nc3cccc(F)c3)c(OCc3ccccc3)c2)cn1]
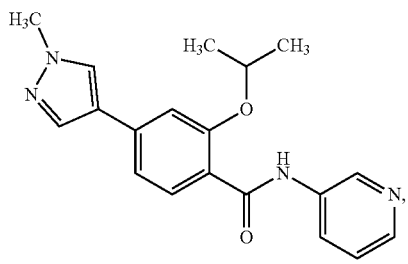 [SMILES: CC(C)Oc1cc(-c2cnn(C)c2)ccc1C(=O)Nc1cccnc1]
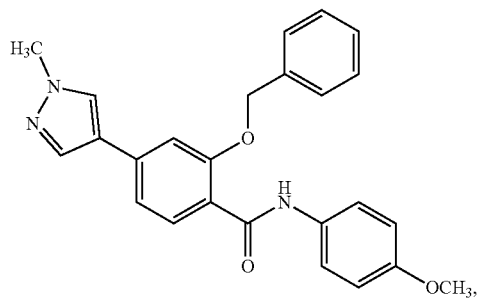 [SMILES: COc1ccc(NC(=O)c2ccc(-c3cnn(C)c3)cc2OCc2ccccc2)cc1]
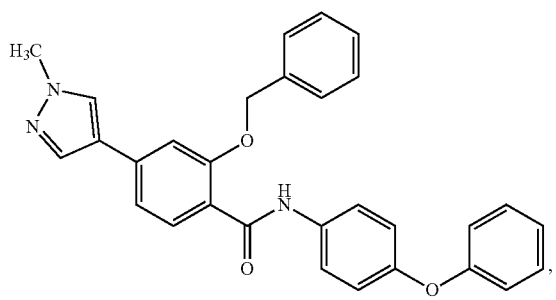 [SMILES: Cn1cc(-c2ccc(C(=O)Nc3ccc(Oc4ccccc4)cc3)c(OCc3ccccc3)c2)cn1]

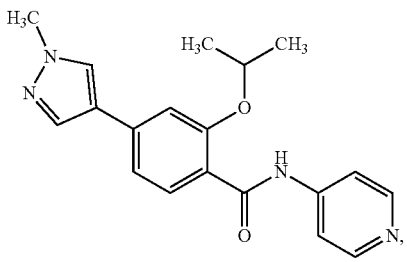 [SMILES: CC(C)Oc1cc(-c2cnn(C)c2)ccc1C(=O)Nc1ccncc1]
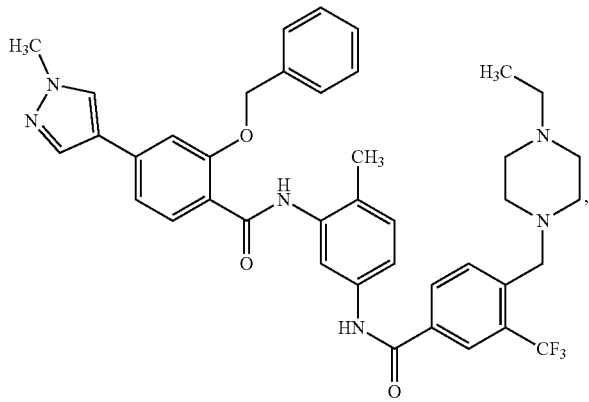 [SMILES: CCN1CCN(Cc2ccc(C(=O)Nc3ccc(C)c(NC(=O)c4ccc(-c5cnn(C)c5)cc4OCc4ccccc4)c3)cc2C(F)(F)F)CC1]
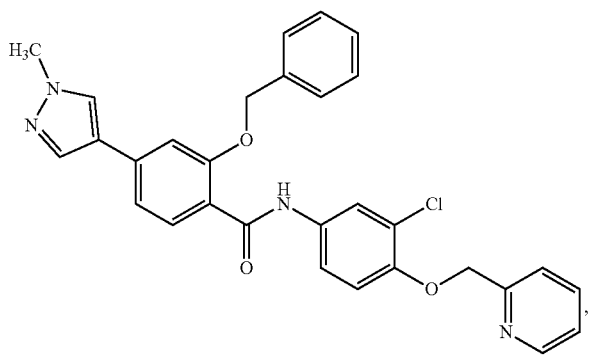 [SMILES: Cn1cc(-c2ccc(C(=O)Nc3ccc(OCc4ccccn4)c(Cl)c3)c(OCc3ccccc3)c2)cn1]
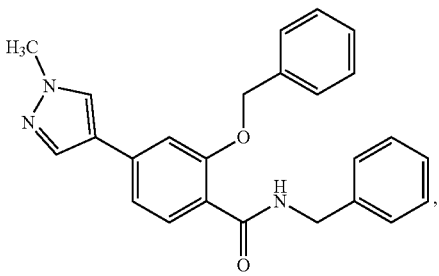 [SMILES: Cn1cc(-c2ccc(C(=O)NCc3ccccc3)c(OCc3ccccc3)c2)cn1]
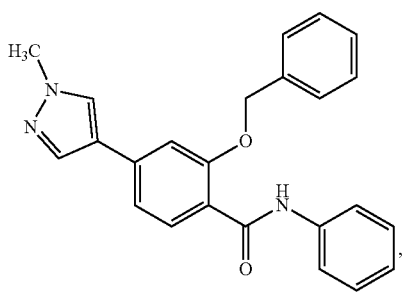

-continued
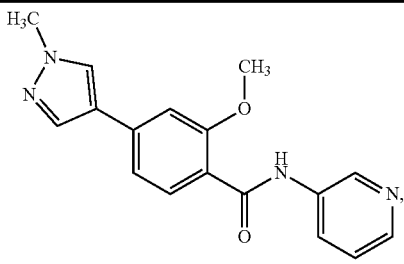
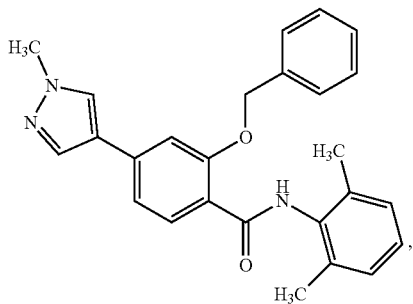
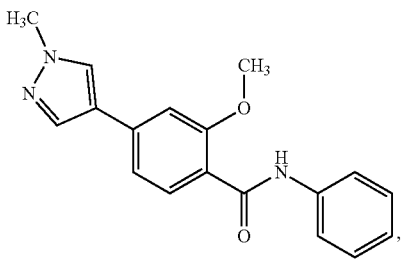 [SMILES: COc1cc(-c2cnn(C)c2)ccc1C(=O)Nc1cccnc1]
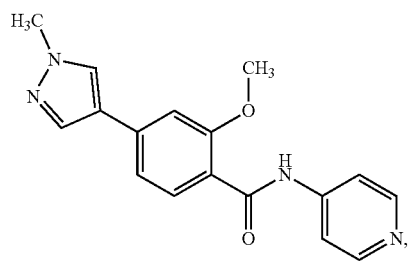 [SMILES: COc1cc(-c2cnn(C)c2)ccc1C(=O)Nc1ccncc1]
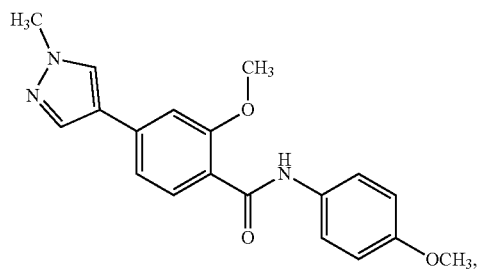 [SMILES: COc1ccc(NC(=O)c2ccc(-c3cnn(C)c3)cc2OC)cc1]
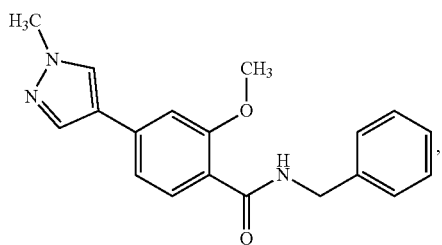 [SMILES: COc1cc(-c2cnn(C)c2)ccc1C(=O)NCc1ccccc1]

-continued
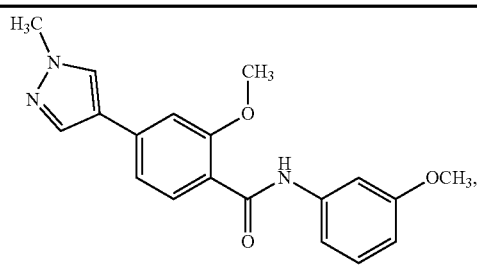
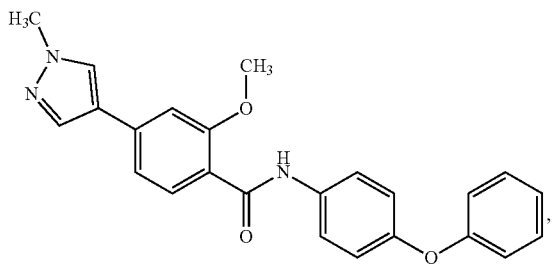 [SMILES: COc1cc(-c2cnn(C)c2)ccc1C(=O)Nc1ccc(Oc2ccccc2)cc1]
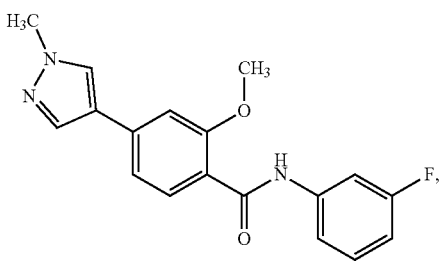 [SMILES: COc1cc(-c2cnn(C)c2)ccc1C(=O)Nc1cccc(F)c1]
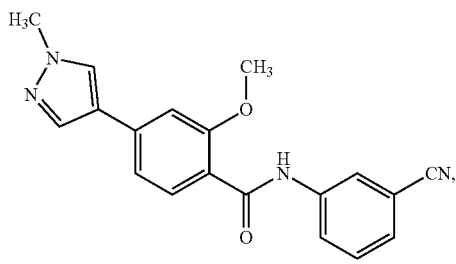 [SMILES: COc1cc(-c2cnn(C)c2)ccc1C(=O)Nc1cccc(C#N)c1]
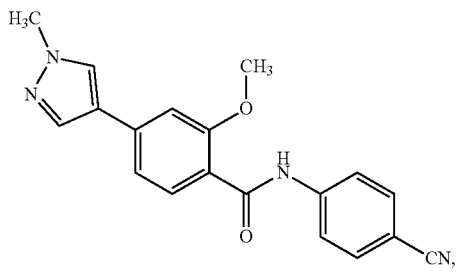 [SMILES: COc1cc(-c2cnn(C)c2)ccc1C(=O)Nc1ccc(C#N)cc1]
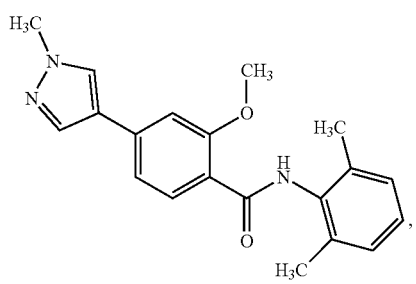 [SMILES: COc1cc(-c2cnn(C)c2)ccc1C(=O)Nc1c(C)cccc1C]

-continued
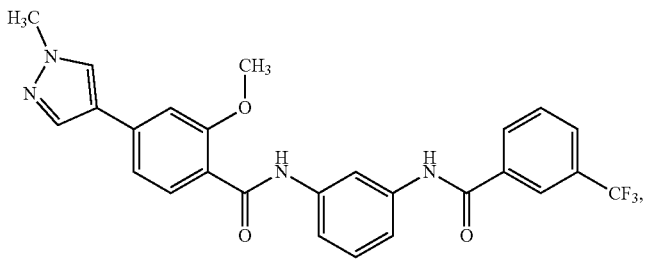 [SMILES: COc1cc(-c2cnn(C)c2)ccc1C(=O)Nc1cccc(NC(=O)c2cccc(C(F)(F)F)c2)c1]
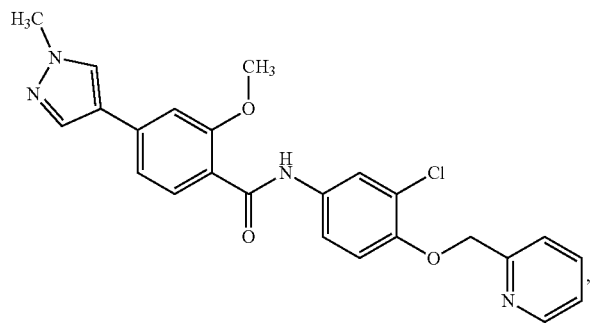 [SMILES: COc1cc(-c2cnn(C)c2)ccc1C(=O)Nc1ccc(OCc2ccccn2)c(Cl)c1]
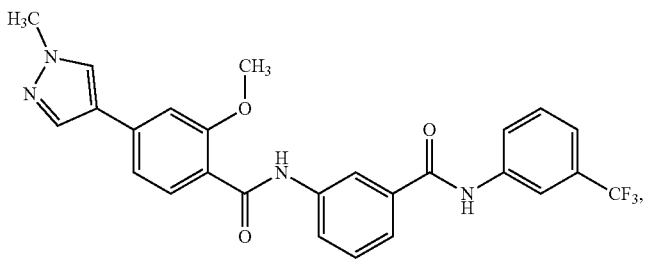 [SMILES: COc1cc(-c2cnn(C)c2)ccc1C(=O)Nc1cccc(C(=O)Nc2cccc(C(F)(F)F)c2)c1]
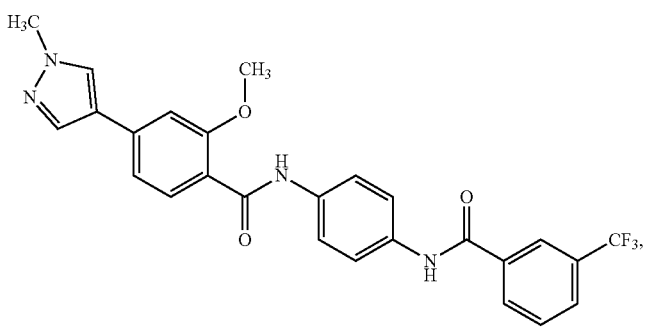 [SMILES: COc1cc(-c2cnn(C)c2)ccc1C(=O)Nc1ccc(NC(=O)c2cccc(C(F)(F)F)c2)cc1]
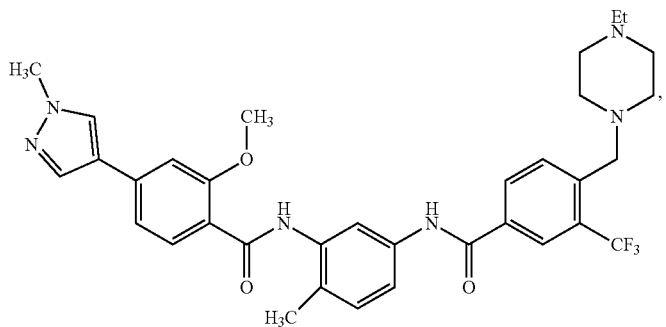

-continued
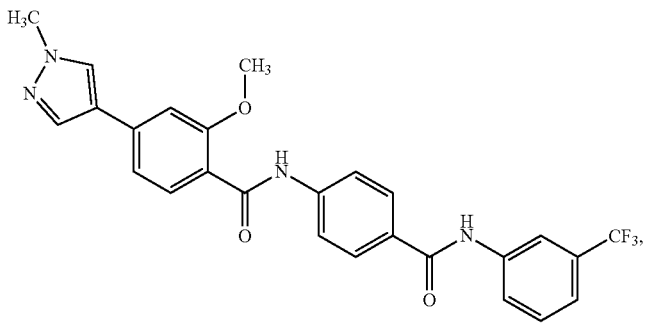 [SMILES: COc1cc(-c2cnn(C)c2)ccc1C(=O)Nc1ccc(C(=O)Nc2cccc(C(F)(F)F)c2)cc1]
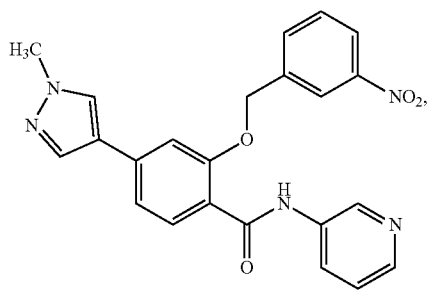 [SMILES: Cn1cc(-c2ccc(C(=O)Nc3cccnc3)c(OCc3cccc([N+](=O)[O-])c3)c2)cn1]
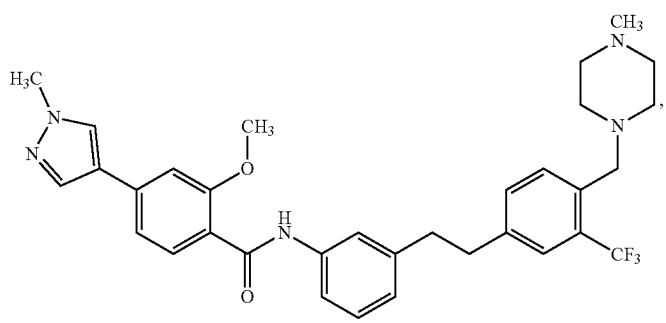
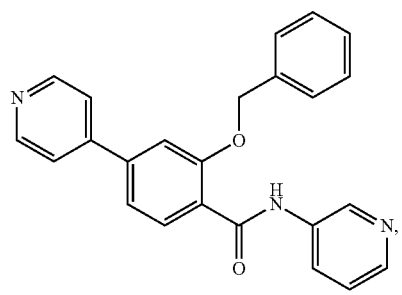 [SMILES: O=C(Nc1cccnc1)c1ccc(-c2ccncc2)cc1OCc1ccccc1]
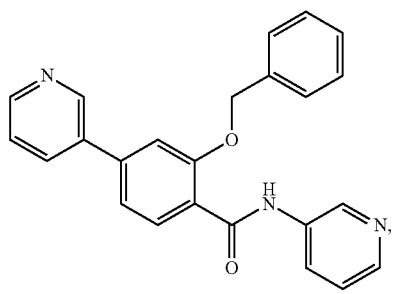 [SMILES: O=C(Nc1cccnc1)c1ccc(-c2cccnc2)cc1OCc1ccccc1]

-continued
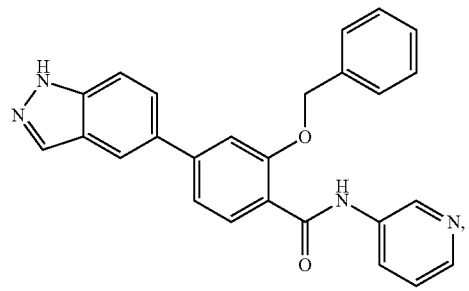 [SMILES: O=C(Nc1cccnc1)c1ccc(-c2ccc3[nH]ncc3c2)cc1OCc1ccccc1]
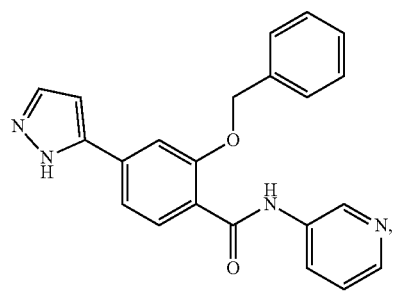 [SMILES: O=C(Nc1cccnc1)c1ccc(-c2ccn[nH]2)cc1OCc1ccccc1]
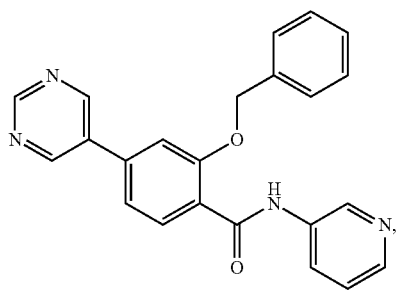 [SMILES: O=C(Nc1cccnc1)c1ccc(-c2cncnc2)cc1OCc1ccccc1]
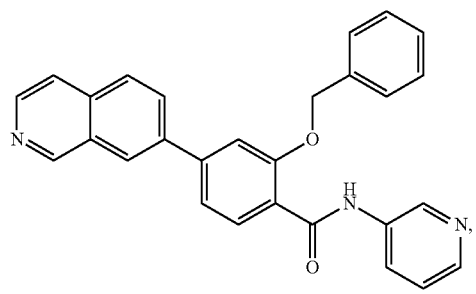 [SMILES: O=C(Nc1cccnc1)c1ccc(-c2ccc3ccncc3c2)cc1OCc1ccccc1]
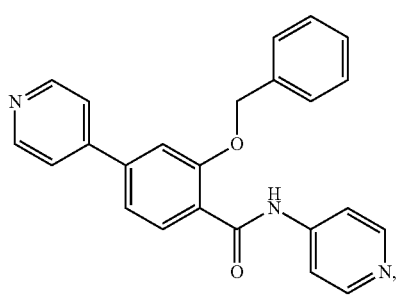 [SMILES: O=C(Nc1ccncc1)c1ccc(-c2ccncc2)cc1OCc1ccccc1]

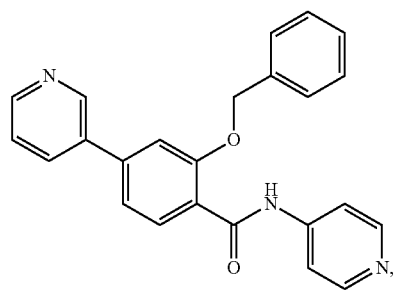 [SMILES: O=C(Nc1ccncc1)c1ccc(-c2cccnc2)cc1OCc1ccccc1]
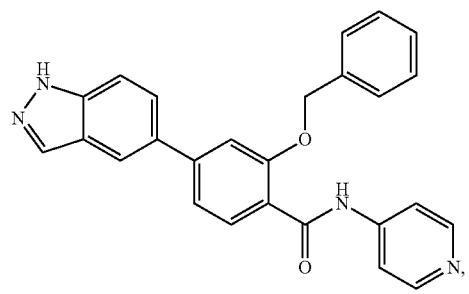 [SMILES: O=C(Nc1ccncc1)c1ccc(-c2ccc3[nH]ncc3c2)cc1OCc1ccccc1]
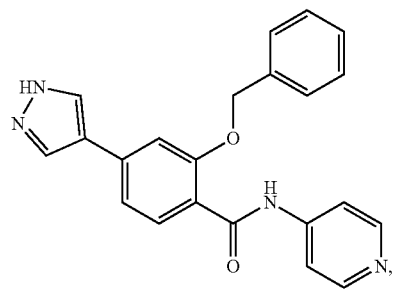 [SMILES: O=C(Nc1ccncc1)c1ccc(-c2cn[nH]c2)cc1OCc1ccccc1]
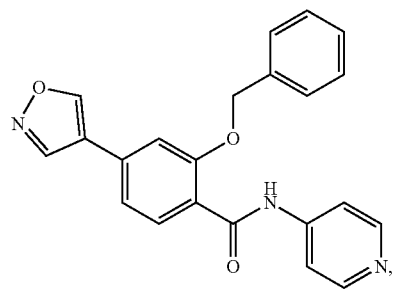 [SMILES: O=C(Nc1ccncc1)c1ccc(-c2cnoc2)cc1OCc1ccccc1]
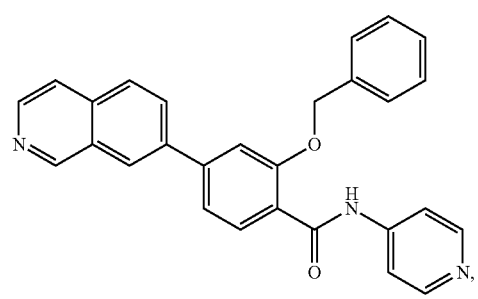 [SMILES: O=C(Nc1ccncc1)c1ccc(-c2ccc3ccncc3c2)cc1OCc1ccccc1]

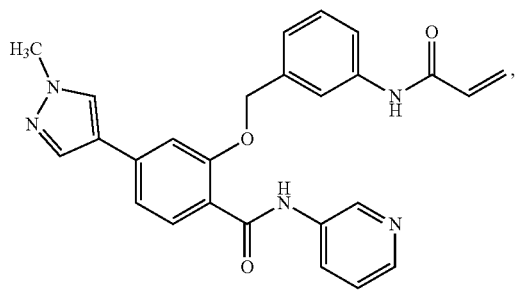 [SMILES: C=CC(=O)Nc1cccc(COc2cc(-c3cnn(C)c3)ccc2C(=O)Nc2cccnc2)c1]
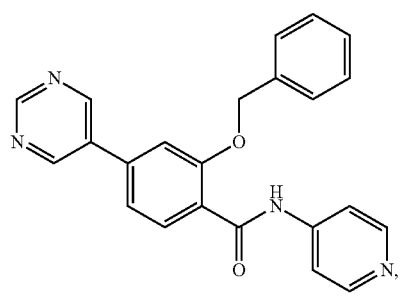 [SMILES: O=C(Nc1ccncc1)c1ccc(-c2cncnc2)cc1OCc1ccccc1]
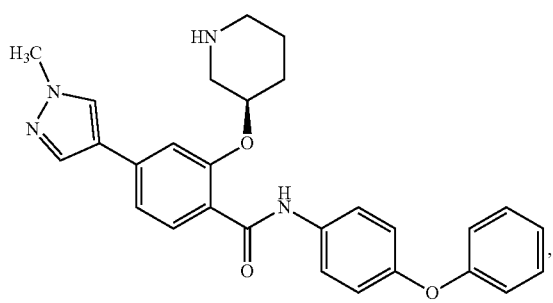 [SMILES: Cn1cc(-c2ccc(C(=O)Nc3ccc(Oc4ccccc4)cc3)c(O[C@@H]3CCCNC3)c2)cn1]
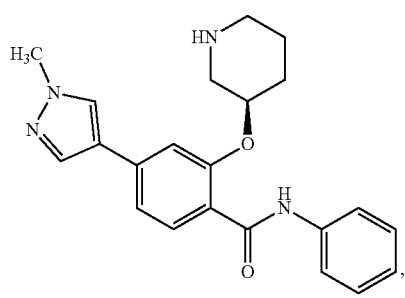
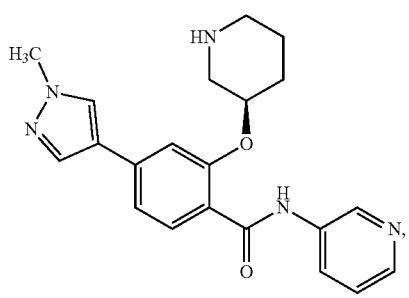 [SMILES: Cn1cc(-c2ccc(C(=O)Nc3cccnc3)c(O[C@@H]3CCCNC3)c2)cn1]

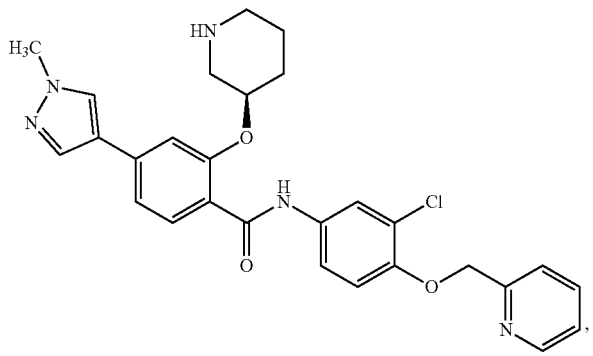 [SMILES: Cn1cc(-c2ccc(C(=O)Nc3ccc(OCc4ccccn4)c(Cl)c3)c(O[C@@H]3CCCNC3)c2)cn1]
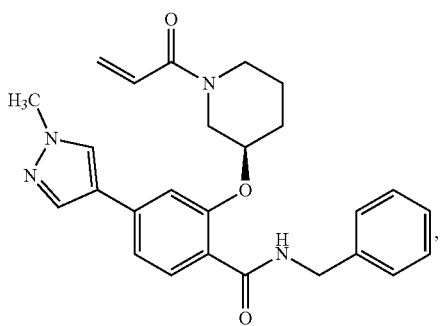 [SMILES: C=CC(=O)N1CCC[C@@H](Oc2cc(-c3cnn(C)c3)ccc2C(=O)NCc2ccccc2)C1]
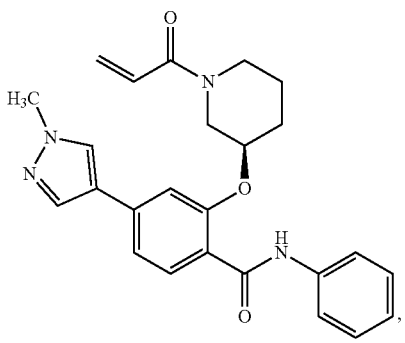
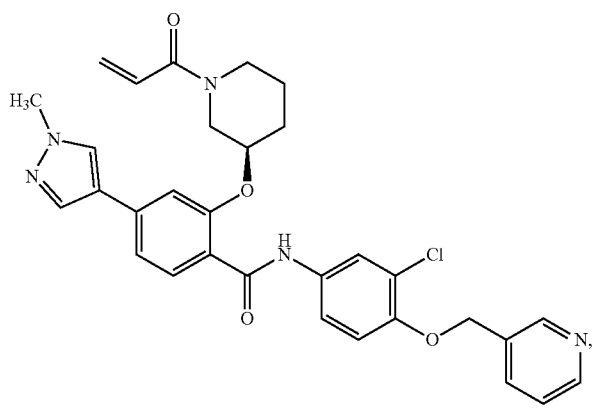 [SMILES: C=CC(=O)N1CCC[C@@H](Oc2cc(-c3cnn(C)c3)ccc2C(=O)Nc2ccc(OCc3cccnc3)c(Cl)c2)C1]

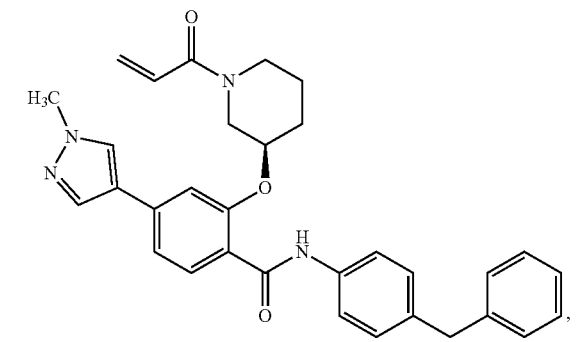 [SMILES: C=CC(=O)N1CCC[C@@H](Oc2cc(-c3cnn(C)c3)ccc2C(=O)Nc2ccc(Cc3ccccc3)cc2)C1]
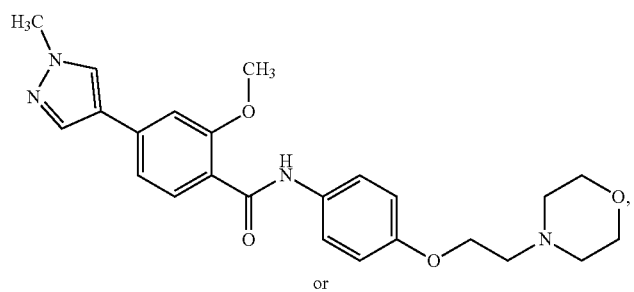
or
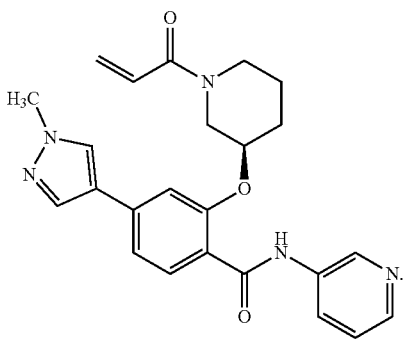 [SMILES: C=CC(=O)N1CCC[C@@H](Oc2cc(-c3cnn(C)c3)ccc2C(=O)Nc2cccnc2)C1]
13. A pharmaceutical composition comprising a compound of claim 1, and a pharmaceutically acceptable carrier.
* * * * *